United States Patent
Day et al.

(10) Patent No.: US 6,380,171 B1
(45) Date of Patent: *Apr. 30, 2002

(54) PRO-PROTEIN CONVERTING ENZYME

(75) Inventors: Robert Day, Sainte-Dorothée; Nabil G. Seidah, Iles-des-Soeurs; Rémi Martel; Michel Chrétien, both of Montréal; Tim Reudelhuber, Baie d'Urfé ; Guy LeClerc, Rosemère, all of (CA)

(73) Assignees: Clinical Research Institute of Montreal; Universite de Montreal; Centre hospitalier de l'Universite de Montreal, all of Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,555

(22) PCT Filed: Jul. 25, 1997

(86) PCT No.: PCT/CA97/00535

§ 371 Date: Sep. 13, 1999

§ 102(e) Date: Sep. 13, 1999

(87) PCT Pub. No.: WO98/04686

PCT Pub. Date: Feb. 5, 1998

Related U.S. Application Data

(60) Provisional application No. 60/021,008, filed on Jul. 26, 1996.

(30) Foreign Application Priority Data

Apr. 25, 1997 (CA) .............................................. 2203745

(51) Int. Cl.[7] ........................ A61K 31/70; A01N 43/04; C12Q 1/68; C07H 21/04
(52) U.S. Cl. ............................. 514/44; 435/6; 435/325; 435/375; 536/23.1; 536/24.5
(58) Field of Search ............................... 536/23.1, 24.5; 435/6, 325, 91.1, 23, 375; 514/44

(56) References Cited

U.S. PATENT DOCUMENTS 5,866,351 A * 2/1999 Franzusoff et al. ........... 435/23

FOREIGN PATENT DOCUMENTS

WO    WO94 15945    6/1994

OTHER PUBLICATIONS

C. Haléne et al., "Specific Regulation of Gene Expression by Antisense, Sense and Antigene Nucleic Acids", Biochimica et Biophysica Acts, Jan. 1990.

T. Nakagawa et al., "Identification and Functional Expression of a New Member of the Mammalian Kex2–Like Processing Endoprotease Family: Its Striking Structural Similarity to PACE4", J. Biochem vol. 2, 132–135 (1993).

J. Lusson et al., cNA Structure of the Mouse and Rat Subtilisin/Kexin–like PC5: A Candidate Proprotein Convertase expressed in Endocrine and Nonendocrine cells, Proc. Natl. Acad. Sci. Jul. 1993.

C. Mercure et al., Prohormaone Convertase PC5 is a Candidate Prociessing Enzyme for Prorenin in Human Adrenal Cortex, *Hypertension*, Oct. 1996.

L. Miranda et al. , "Isolation of the Human PC6 Gene Encoding the Putative Host Protease for HIV–1 gp160 Processing in CD4+T Lymphocytes", Proc. Natl. Acad. Sci. Jul. 1996.

E. Decroly et al., "The Convertases Furin and PC1 can Both Cleave the Human Immunodeficiency Virus (HIV–1) Envelope Glycoprotein gp160 into gp120 (HIV–1 SU) and gp41 (HIV–1 TM)", J. Bio. Chem., Apr. 22, 1994.

* cited by examiner

Primary Examiner—John L. LeGuyader
Assistant Examiner—Janet L. Epps
(74) Attorney, Agent, or Firm—Quarles & Brady LLP

(57) ABSTRACT

The present invention relates to the cloning of human pro-protein converting enzyme 5 (PC5) CDNA isolated from human adrenal gland messenger RNA. Additionally, this invention relates to a method for reducing restenosis occurring at an injured vascular site comprising delivering to the injured site an antisense nucleic acid to suppress the expression of human PC5.

3 Claims, 26 Drawing Sheets

PC5A 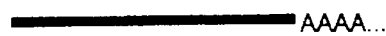
PC5B 
RT-PCR 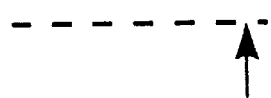
mPC5sp    =
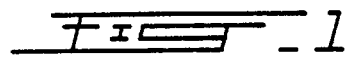
1 Kb
FIG_1

```
ATGGACTGGGGACTGGGGAACCGCTGCAGCCGCCCCGGGAGGCGGGACCTGCTGTGTGTGCTGGCTCTGCTCGGGGGATGTCTGCTCCCCGTGTGTCGGACGCGTGTACACCAACCAC  120
 M  D  W  G  L  G  N  R  C  S  R  P  G  R  R  D  L  L  C  V  L  A  L  L  G  G  C  L  L  P  V  C  R  T  R  V  Y  T  N  H
TGGGCAGTGCAAAATCGCCCGGGGGCTTCCCGGAGGCCAATAGGATACGGGCAATAGGACATAGGGACACTACCACTTCTACCATAGCAGG                                 240
 W  A  V  K  I  A  G  F  P  E  A  N  R  I  A  S  K  Y  G  F  I  N  I  G  Q  I  G  A  L  K  D  Y  Y  H  E  Y  H  S  R
ACGGATTAAAAGGTCAGTTATCTCGAGCAGGGACCCACAGTTTCATTTCAATGAACCAAAGGTGAATGACTGAATCCAACAGCAAGTGATCAAAAAGCGGACAAAGAGGGATTATGACTTC  360
 T  I  K  R  S  V  I  S  S  R  G  T  H  S  F  I  S  M  E  P  K  V  E  W  I  Q  Q  V  V  K  K  R  T  K  R  D  Y  D  F
AGTCGTGCCCAGTCTACCTATTCAATGACCCAAGTGCCCAGCATGTGGTATATGCACTGTGACAATATCCCGCAGTCTGACATGAATATCGAAGGAGCCTGGAAGAGA                480
 S  R  A  Q  S  T  Y  F  N  D  P  K  W  P  S  M  W  Y  M  H  C  S  D  N  T  H  P  C  Q  S  D  M  N  I  E  G  A  W  K  R
GGCTACACGGGGAAAGAACATTGTGTCACTATCCTGGATGACGAAGTGAGAACATCCAGATGCAGAACTACAAAACTGAACGCATGGAGAGAAGTGGACGTGAAGTTGGACGTGAATGACTTG  600
 G  Y  T  G  K  N  I  V  V  T  I  L  D  D  G  I  E  R  T  H  P  D  L  M  Q  N  Y  D  A  L  A  S  C  D  V  N  G  N  D  L
GACCCAAATGCCTCGTTATGATGAAGCAAGCAACGAGAACAAGCATGGAACCCGCTGCAAAACAATTGCAGGCGAAGTAGCTAGCTTCAACCCCCAGCACGTTCACATTTACAGCGCCAAG   720
 D  P  M  P  R  Y  D  A  S  N  E  N  K  H  G  T  R  C  A  G  E  V  A  A  A  A  N  N  S  H  C  T  V  G  I  A  F  N  A  K
ATCGGAGGAGTGCGCATGCTGGACGGAGATGTCACGGACATGGTTGAAGCAAAATCGGGGTTAGAATGGGCGGAGAGGCCTCGGGCATCTGAAATGTGGAAGGAGCAAGATGATGATGGA  840
 I  G  G  V  R  M  L  D  G  D  V  T  D  M  V  E  A  K  S  V  S  E  N  P  Q  H  V  H  I  Y  S  A  S  W  G  P  D  D  D  G
AAGACTGTGGACGGACCAGCCCCTCTGACCCGCCAAGCCTTTGAAAACGGGTTAGAAGAGTGTTCATCCACGTTGGCCACCACC                                        960
 K  T  V  D  G  P  A  P  L  T  R  Q  A  F  E  N  G  V  R  M  G  R  R  G  L  G  S  V  F  V  W  A  S  G  N  G  G  R  S  K
GACCACTGCTCCTGTGATGGCTACAGCAACAGCATCTACACCACCATCTCAGCCCGTCAGCTGAGGACTGACAACCACACCGGGACTTCAGCGTCAGCGCCGATGGCAGCAGGCATCATTGCGCTG  1080
 D  H  C  S  C  D  G  Y  T  N  S  I  Y  T  I  S  I  S  S  T  A  E  S  G  K  K  P  W  Y  L  E  E  C  S  S  T  L  A  T
TACAGCAGCGGGAGTGCTAGATGGACAAGAAAAATCATCACTACAGATCTGAGGCAGCGCTGTACAGACAATCACACTGGGACATCTGCATCAGCCCCAATGGCAGCAGCAGGCATCATTGCGCTG  1200
 Y  S  S  G  E  S  Y  D  K  K  I  I  T  T  D  L  R  Q  R  C  T  D  N  H  T  G  T  S  A  S  A  P  M  A  A  G  I  I  A  L
GCCCTGGAAGCCAATCCGTTTCTGACCTGGAGAGGTGTGCTCACAGACTGTACAGATGCTACGATGCAGCATGTCAACGCGGTTTAAGGGTG                              1320
 A  L  E  A  N  P  F  L  T  W  R  D  V  Q  H  V  I  V  R  T  S  R  A  G  H  L  N  A  N  D  W  K  T  N  A  A  G  F  K  V
AGCCATCTTTATGGATTGATGACTGAGGCGGAGAGCCATGGTGGAGGCAGAGAAGTGGACCGTGTGTGTGTGAATCCGGAGCACACCGTTCCCGCGCCCCAGCACGTTGGACGTGTGGAATCCGGACCGTGTCAAGACA  1440
 S  H  L  Y  G  F  G  L  M  D  A  E  A  M  V  E  A  E  K  W  T  T  V  P  R  Q  H  V  C  V  E  S  T  D  R  Q  I  K  T
```

FIG. 2A

```
ATCCGCCCTAACAGTGCAGTGGCTCCATCTACAAAGCTTCAGGCTGTCCTGGATAACCGGCCATGTCAACTACCTGGAGCACGTCGTTGTGCGCATCACCATCACCCACCCAGG  1560
 I  R  P  N  S  A  V  R  S  I  Y  K  A  S  G  C  S  D  N  P  N  R  H  V  N  Y  L  E  H  V  V  V  R  I  T  I  T  H  P  R

AGAGGAGACCTGGCCATCTACTACCTGCCTCGCCTCTGACCCTCTGAACTAGTCTCAGTCTCTGAAGTTTATGATCACTCCATGGAAGATTCAAAAACTGGAGTTCATGACCATTCAT  1680
 R  G  D  L  A  I  Y  L  T  S  P  S  G  T  R  S  Q  L  L  A  N  R  L  F  D  H  S  M  E  G  F  K  N  W  E  F  M  T  I  H

TGCTGGGGAGAAAGAGCTGCTGGTGACTGGGTCCTTGAAGTTTATGATACTCCTCAGCTCAGGAACTTTAAGAACTTTAAGAATTCCAGTAATTGAAGACTTCCAGTAAATTGAAAGAATGGTCTTTGGTCCTCTACGGCACC  1800
 C  W  G  E  R  A  A  G  D  W  V  L  E  V  Y  D  T  P  S  Q  L  R  N  F  K  T  P  G  K  L  K  E  W  S  L  V  L  Y  G  T

TCCGTGCAGCCATATTCAACAATGAATTTCCGAAAGTGGAACGGTTCCGTACTAGCCGAGTTGAAGACCCCGACTATGGCACAGAGGATTATGCAGGTCCCTGCGACCCT  1920
 S  V  Q  P  Y  S  P  T  N  E  F  P  K  V  E  R  F  R  Y  S  R  V  E  D  P  T  D  D  Y  G  T  E  D  Y  A  G  P  C  D  P

GAGTGCAGTGAGGTTGGCTGTGACGGGCCAGGACCTGATCACTGCAATGACTGTCTGCACTACTACTACTACAAGATCATGTCTCCAGTCTGTGACCAATGTGAGCCCTGGCCAC  2040
 E  C  S  E  V  G  C  D  G  P  P  D  H  C  N  D  C  L  H  Y  Y  Y  K  I  M  S  C  P  P  G  H

TACCACCGCCAGAAGCGCTGCAGGAAGTGTGCCCCCAACTGTGAGTCCTGCTTTGGAGCCATGGGCGATCAGTGTATGAGCTGCAAATATGGACTACTTTCTGAATGAAGAAACCAAC  2160
 Y  H  A  D  K  K  R  C  R  K  C  A  P  N  C  E  S  C  F  G  S  H  G  D  Q  C  M  S  C  K  Y  G  Y  F  L  N  E  E  T  N

AGTGTGTTACTCACTGCCCTGATGGGTCCCTGCATATCGCCAGAAGAATACCAAGAACAATGCCAAGAACATGCTGAATTCACTGTACAGAATGTAGGGAT  2280
 S  C  V  T  H  C  P  D  G  S  Y  Q  D  T  K  K  N  L  C  R  K  C  S  E  N  C  K  T  C  T  E  F  H  N  C  T  E  C  R  D

GGGTTAAGCTGTGCACTGCAGCGATCCGGGGATCCGGTCTGTCTGTGAAGATGACGGTATTCAAGGACGTATTCAACGGGGACTGTCAGCCTCACAGGTTTGAATGTGCTCAGGAGCTGAT  2400
 G  L  S  L  Q  G  S  R  C  S  V  S  C  E  D  G  R  Y  F  N  G  Q  D  C  Q  P  H  R  F  C  A  T  C  A  G  A  D

GGGTGCATTAACTGCACAGAGGGCTACTTCATGGAGGATGGGAGATGCGTGCAAAGCTGTGTAGTACGTCAGAGCTGCAGCATCAGTTATTACTTTGACCACTCTTCAGAGAATGGATACAAAATCCTGCAAAAATGT  2520
 G  C  I  N  C  T  E  G  Y  F  M  E  D  G  R  C  V  Q  S  C  V  S  S  I  S  Y  Y  F  D  H  S  S  E  N  G  Y  K  S  C  K  C

GATATCAGTTGTTTGACGTGCAATGGCCAGGATTCAAGAACTGTACAAGCTGCCCTAGTGGGCTATCTTGACTTAGGAATGTGTCAAATGGTCAAGGATGCAACGGAA  2640
 D  I  S  C  L  T  C  N  G  P  G  F  K  N  C  T  S  C  P  S  G  Y  L  L  D  L  G  M  C  Q  M  G  A  I  C  K  D  A  T  E

GAGTCCTGGGCGGAAGGAGGCTTCTATGCTTGTGAAAAGAACATTGTGCTCAACAACTTGTCTTCAACAATGTGTGCAAAACATGTACATTTCAAGGCTGAGCAGCCATCTTA  2760
 E  S  W  A  E  G  G  F  C  M  L  V  K  K  N  L  C  Q  R  K  V  L  Q  Q  L  C  C  K  T  C  T  F  Q  G  STOP

GATTTCTTGTTCCTGTAGACTTATAGATTATTCCATATATTATAAAAGAAAAAAAAA
```

FIG.-2B

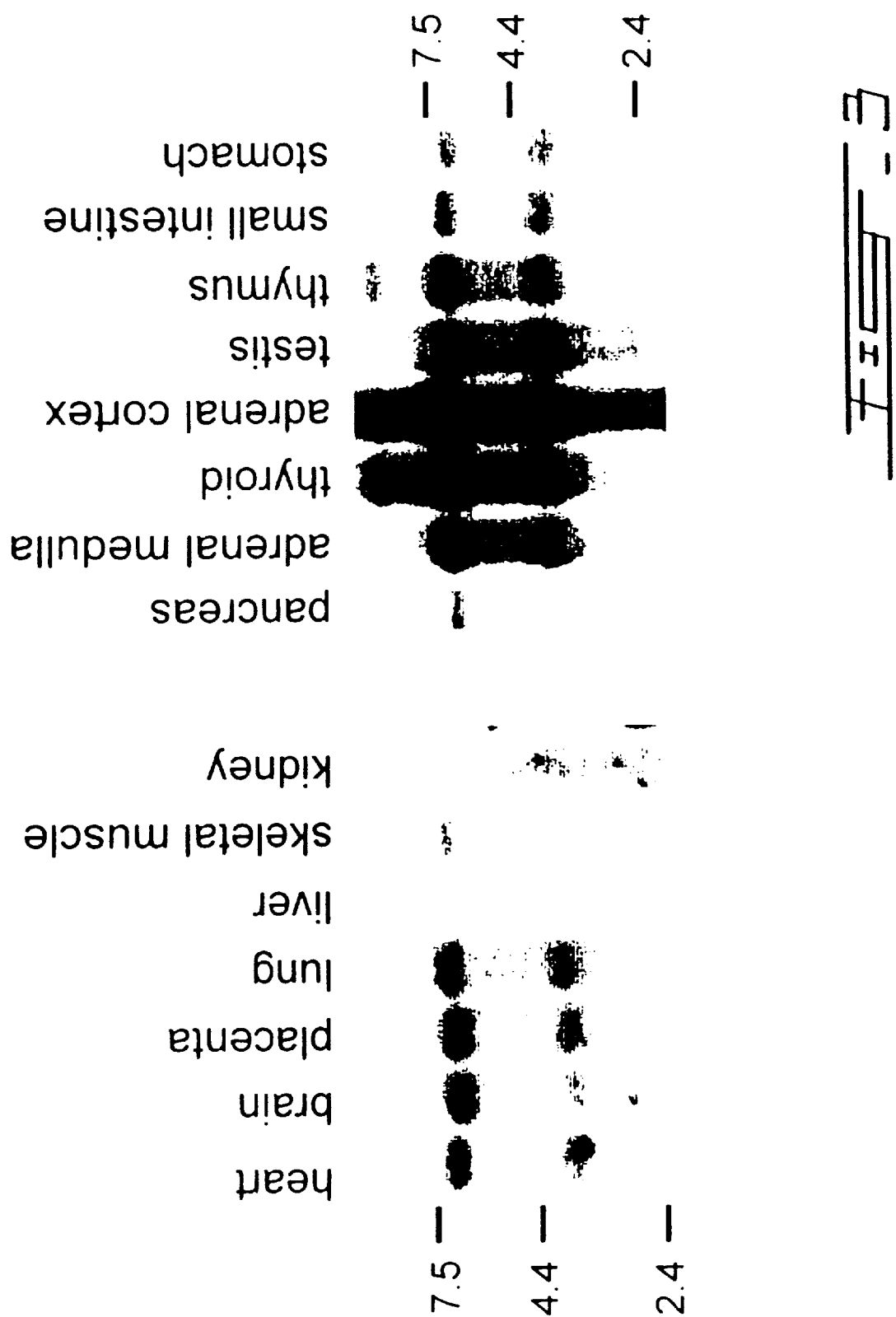

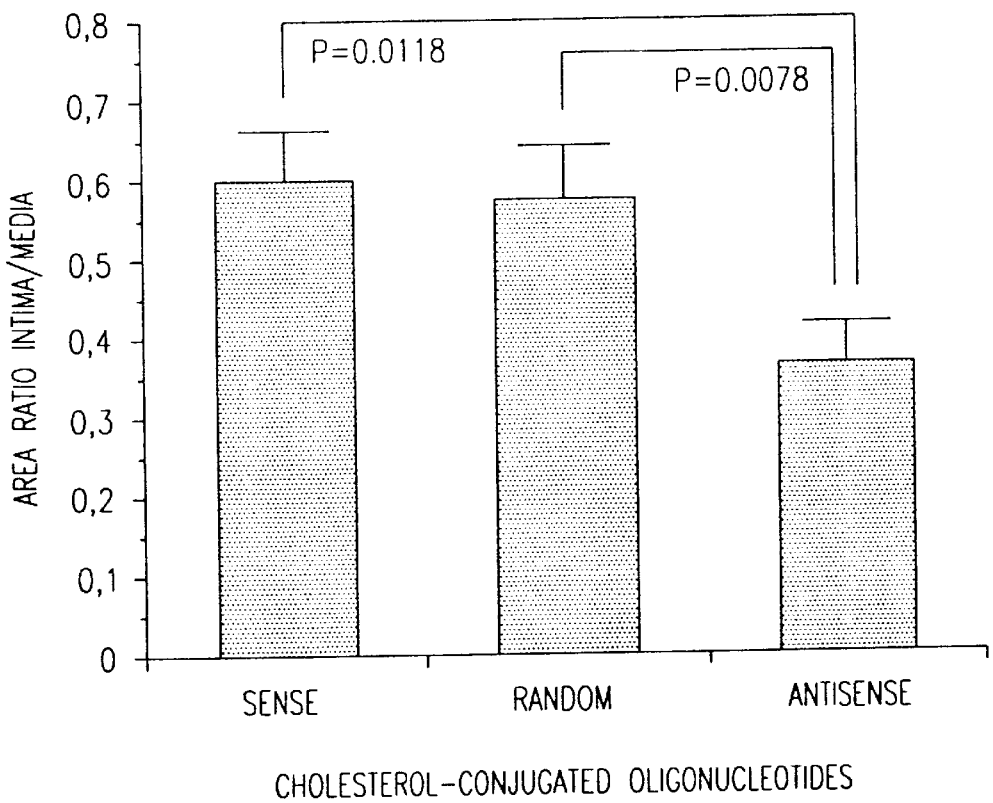
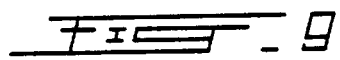
FIG. 9
| | PC1 | PC2 | PC5 | PC7 | Furin |
|---|---|---|---|---|---|
| Number of Slide | n=31 | n=29 | n=25 | n=27 | n=30 |
| Mean Positivity (Scale 0-3) | 0.29 | 2.03 | 2.08 | 1.19 | 1.08 |
| SD | 0.46 | 0.61 | 0.62 | 1.04 | 1.07 |
| % (+) Slide | 29.0 | 96.6 | 96.0 | 63.0 | 60 |
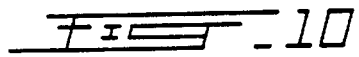
FIG. 10

```
Miranda1  AGCGTCGGGACCATGGATTGGGGATTGGGGGAACCGCTGCAGCCCGCGGG   50
                                    ATGGACTGGGAACTGGGAACCGCTGCAGCCCGCGGG   38
IRCM      1 ..........

51 ACGGCGGGACCTGCTGCGTGCCTGGCACTGCTCCGCCGGCTGTCTGCTCC  100
         39 ACGGGGGATCTGCTGCTGTGCCTGGCACTGCTCCGGGGCTGCTGCTCC    88

101 CGGTATGCCGGACGCGCGTCTACACCAACCACTGGGCAGTGAAGATCGCC  150
         89 CCGTGTGCCGGACGCGCGTCTACACCAACCACTGGGCAGTCAAAATCGCC  138

151 GGGGCTTCGGCGGAGGCAGATCGCATAGCCCAGCAAGTACGGATTCATCAA 200
        139 GGGGCTTCCCGGAGGCCAACCGTATCGCCAGCAAGTACGGATTCATCAA  188

201 CGTAGGACAGATCGGTGCACTGAAGGACTACTATCACTTCTACCATAGTA  250
```

FIG. 11A

```
189  CATAGGACAGATAGGGGCCCTGAAGGACTACTACCACTTCTACCATAGCA  238
     ||||||||||||||||||||||||||||||||||||||||||||||||||
251  GGACCATTAAAAGGTCTGTTCTCTCGAGCAGAGGAACCCACAGTTTCATT  300
     || ||  ||| ||||  || |||||||||||| ||||||||||||||||
239  GGACGATTAAAAGGTCAGTTTATCTCGAGCAGAGGGACCCACAGTTTCATT  288

301  TCAATGGAACCAAAGGTGGAGTGGATCCAAACAGCAAGTGGTGAAAAAAG  350
     |||||||||||||||||||| ||||||||| |||||||||||  |||||
289  TCAATGGAACCAAAGGTGGAATGGATCCAAACAGCAAGTGGTAAAAAAGCG  338

351  AACCAAGAGGGATTATGACCTCAGCCATGCCCAGTCAACCTACTTCAATG  400
     |||||||||| ||||||||||| |||| || |||||||| |||||||||
339  GACAAAGAGGGATTATGACTTCAGTCATGCCCAGTCCAGTCTACCTATTTCAATG  388

401  ATCCCAAGTGGCCAGCCATGTGGTACATGTGGTACACTGTAGCGACAATACACAT  450
     ||||||||| ||||||||||||| |||||| ||||||||||||||||||
389  ATCCCAAGTGGCCCAGCATGTGGTATATGGTCACTGCAGTGACAATACACAT  438

451  CCCTGCCAGTCTGACATGAATATCGAAGAGCCTGGAAGAGAGGCTACAC  500
     ||||||||||||||||||||||||||||||||||||||||||||||||
```

FIG.-11B

```
439  CCCTGCCAGTCTGACATGAATATCGAAGGAGCCTGGAAGAGAGGCTACAC  488
     ||||||||||||||||||||||||||||||||||||||||||||||||||
501  GGGAAAGAACATTGTGGTCACTATCCCTGGATGACGGAATTGAGAGAACCC  550
     ||||||||||||||||||||||||||||||||||||||||||||||||||
489  GGGAAAGAACATTGTGGTCACTATCCCTGGATGACGGAATTGAGAGAACCC  538
     .                                                .
551  ATCCAGATCTGATGCAAAACTACGATGCTCTGGCAAGTTGCGACGTGAAT  600
     ||||||||||||||||||||||||||||||||||||||||||||||||||
539  ATCCAGATCTGATGCAAAACTACGATGCTCTGGCAAGTTGCGACGTGAAT  588
     .                                                .
601  GGGAATGACTTGGACCCAATGCCCTCGTTATGATGCAAGCAACGAGAACAA  650
     ||||||||||||| ||||||||||||||||||||||||||||||||||||
589  GGGAATGACTTGGACCCAATGCCCTCGTTATGATGCAAGCAACGAGAACAA  638
     .                                                .
651  GCATGGGACTCGCTGTGCTGGAGAAGTGGCAGCCGCTGCAAACAATTCGC  700
     ||||||||||||||||||||||||||||||||||||||||||||||||||
639  GCATGGGACTCGCTGTGCTGGAGAAGTGGCAGCCGCTGCAAACAATTCGC  688
     .                                                .
701  ACTGCACAGTCGGAATTGCTTTCAACGCCAAGATCGGAGGAGTGCCGAATG  750
     ||||||||||||||||||||||||||||||||||||||||||||||||||
```

FIG-11C

```
689  ACTGCACAGTCGGAATTGCTTTCAACGCCAAGATCGGAGGAGTGCGAATG  738
     |||||||||||||||||||||||||||||||||||||||||||||||||
751  CTGGACGGAGATGTCACGGACATGGTTGAAGCAAAATCAGTTAGCTTCAA  800
     |||||||||||||||||||||||||||||||||||||||||||||||||
739  CTGGACGGAGATGTCACGGACATGGTTGAAGCAAAATCAGTTAGCTTCAA  788
     |||||||||||||||||||||||||||||||||||||||||||||||||
801  CCCCCAGCACGTGCACATTTACAGCGCCAGCTGGGCCCGGATGATGATG  850
     |||||||||||||||||||||||||||||||||||||||||||||||||
789  CCCCCAGCACGTGCACATTTACAGCGCCAGCTGGGCCCGGATGATGATG  838
     |||||||||||||||||||||||||||||||||||||||||||||||||
851  GCAAGACTGTGGACGGACCCCCCTCACCCGGCAAGCCTTTGAAAAC  900
     |||||||||||||||||||||||||||||||||||||||||||||||||
839  GCAAGACTGTGGACGGACCCCCCCTCACCCGGCAAGCCTTTGAAAAC  888
     |||||||||||||||||||||||||||||||||||||||||||||||||
901  GGCGTTAGAATGGGGCGGAGAGGCCTCGGCTCTGTGTTTGTTTGGGCATC  950
     |||||||||||||||||||||||||||||||||||||||||||||||||
889  GGCGTTAGAATGGGGCGGAGAGGCCTCGGCTCTGTGTTTGTTTGGGCATC  938
     |||||||||||||||||||||||||||||||||||||||||||||||||
951  TGGAAATGGTGGAAGGAGCAAAGACCACTGCTCCCTGTGATGGCTACACCA 1000
     |||||||||||||||||||||||||||||||||||||||||||||||||
```

FIG. 11D

```
 939  TGGAAATGGTGGAAGGAGCAAAAGACCACTGCTCCTGTGATGGCTACACCA   988
      ||||||||||||||||||||||||||||||||||||||||||||||||||
1001  ACAGCATCTACACCATCTCCATCAGCAGCACTGCAGAAAGCGGAAAGAAA  1050
      |||||||||||||||||||||||||||||||||||||||||||||||||
 989  ACAGCATCTACACCATCTCCATCAGCAGCACTGCAGAAAGCGGAAAGAAA  1038

1051  CCTTGGTACCTGGAAGAGTGTTCATCCCACGGCCACAACCTACAGCAG    1100
      ||||||||||||||||||||||||||||||||||||||||||||||||
1039  CCTTGGTACCTGGAAGAGTGTTCATCCCACGGCCACAACCTACAGCAG    1088

1101  CGGGGAGTCCTACGATAAGAAAATCATCACTACAGATCTGAGGCAGCGTT  1150
      ||||||||||||||||||||||||||||||||||||||||||||||||||
1089  CGGGGAGTCCTACGATAAGAAAATCATCACTACAGATCTGAGGCAGCGTT  1138

1151  GCACGGACAACCACCACTGGGACGTCAGCCCTCAGCCCCCATGGCTGCAGGC  1200
      ||||||||||||||||||||||||||||||||||||||||||||||||||
1139  GCACGGACAACCACCACTGGGACGTCAGCCCTCAGCCCCCATGGCTGCAGGC  1188

1201  ATCATTGCGCTGGCCCTGGAAGCCAATCCGTTTCTGACCTGGAGAGACGT  1250
      ||||||||||||||||||||||||||||||||||||||||||||||||||
```

FIG-11E

```
1189 ATCATTGCGCTGGCCCTGGAAGCCAATCCGTTTCTGACCTGGAGAGACGT 1238
     ||||||||||||||||||||||||||||||||||||||||||||||||||
1251 ACAGCATGTTATTGTCAGGACTTCCCGTGCGGGACATTTGAACGCTAATG 1300
     ||||||||||||||||||||||||||||||||||||||||||||||||||
1239 ACAGCATGTTATTGTCAGGACTTCCCGTGCGGGACATTTGAACGCTAATG 1288
     ||||||||||||||||||||||||||||||||||||||||||||||||||
1301 ACTGGAAAACCAATGCTGCTGGTTTTAAGGTGAGCCATCTTTATGGATTT 1350
     ||||||||||||||||||||||||||||||||||||||||||||||||||
1289 ACTGGAAAACCAATGCTGCTGGTTTTAAGGTGAGCCATCTTTATGGATTT 1338
     ||||||||||||||||||||||||||||||||||||||||||||||||||
1351 GGACTGATGGACGCAGAAGCCATGGTGATGGAGGCAGAGAAGTGGACCAC 1400
     ||||||||||||||||||||||||||||||||||||||||||||||||||
1339 GGACTGATGGACGCAGAAGCCATGGTGATGGAGGCAGAGAAGTGGACCAC 1388
     ||||||||||||||||||||||||||||||||||||||||||||||||||
1401 CGTTCCCCGGCAGCACGTGTGTGTGGAGAGCACAGACCGACAAATCAAGA 1450
     ||||||||||||||||||||||||||||||||||||||||||||||||||
1389 CGTTCCCCGGCAGCACGTGTGTGTGGAGAGCACAGACCGACAAATCAAGA 1438
     ||||||||||||||||||||||||||||||||||||||||||||||||||
1451 CAATCCGCCCTAACAGTGCAGTGCGCTCCATCTACAAAGCTTCAGGCTGC 1500
     ||||||||||||||||||||||||||||||||||||||||||||||||||
```

FIG-11F

```
1439 CAATCCGGCCCTAACAGTGCAGTGCGCTCCATCTACAAAGCTTCAGGCTGC 1488
          ||||||||||||||||||||||||||||||||||||||||||||||||||
1501 TCGGATAACCCCAACCGCCATGTCAACTACCTGGAGCACGTCGTTGTGCG 1550
          ||||||||||||||||||||||||||||||||||||||||||||||||||
1489 TCGGATAACCCCAACCGCCATGTCAACTACCTGGAGCACGTCGTTGTGCG 1538
          ||||||||||||||||||||||||||||||||||||||||||||||||||
1551 CATCACCATCACCCCACCCCAGGAGAGGAGACCTGGCCATCTACCTGACCT 1600
          ||||||||||||||||||||||||||||||||||||||||||||||||||
1539 CATCACCATCACCCCACCCCAGGAGAGGAGACCTGGCCATCTACCTGACCT 1588
          ||||||||||||||||||||||||||||||||||||||||||||||||||
1601 CGCCCTCTGGAACTAGGTCTCAGCTTTTGGCCAACAGGCTATTTGATCAC 1650
          ||||||||||||||||||||||||||||||||||||||||||||||||||
1589 CGCCCTCTGGAACTAGGTCTCAGCTTTTGGCCAACAGGCTATTTGATCAC 1638
          ||||||||||||||||||||||||||||||||||||||||||||||||||
1651 TCCATGGAAGGATTCAAAAACTGGGAGTTCATGACCATTCATTGCTGGGG 1700
          ||||||||||||||||||||||||||||||||||||||||||||||||||
1639 TCCATGGAAGGATTCAAAAACTGGGAGTTCATGACCATTCATTGCTGGGG 1688
          ||||||||||||||||||||||||||||||||||||||||||||||||||
1701 AGAAAGAGCTGCTGGTGACTGGTCCCTTGAAGTTTATGATACTCCCTCTC 1750
          ||||||||||||||||||||||||||||||||||||||||||||||||||
```

Fig-11G

```
1689  AGAAAGAGCTGCTGGTGACTGGGTCCCTTGAAGTTTATGATACTCCCTCTC  1738
      ||||||||||||||||||||||||||||||||||||||||||||||||||
1751  AGCTAAGGAACTTAAGACTCCAGGTAAATTGAAAGAATGGTCTCTTTGGTC  1800
      ||||||||||||||||||||||||||||||||||||||||||||||||||
1739  AGCTAAGGAACTTAAGACTCCAGGTAAATTGAAAGAATGGTCTTTGGTC   1788
      ||||||||||||||||||||||||||||||||||||||||||||||||||
1801  CTCTACGGCACCTCCGTGCGGCCATATTCACCAACCAATGAATTTCCGAA  1850
      ||||||||||||||||||||||||||||||||||||||||||||||||||
1789  CTCTACGGCACCTCCGTGCCAGCCATATTCACCAACCAATGAATTTCCGAA 1838
      ||||||||||||||||||||||||||||||||||||||||||||||||||
1851  AGTGGAACGGTTCCGCTATAGCCCGAGTTGAAGACCCCACAGACGACTATG 1900
      ||||||||||||||||||||||||||||||||||||||||||||||||||
1839  AGTGGAACGGTTCCGCTATAGCCCGAGTTGAAGACCCCACAGACGACTATG 1888
      ||||||||||||||||||||||||||||||||||||||||||||||||||
1901  GCACAGAGGATTATGCAGGTCCCCTGCCGACCCTGAGTGCAGTGAGGTTGGC 1950
      ||||||||||||||||||||||||||||||||||||||||||||||||||
1889  GCACAGAGGATTATGCAGGTCCCCTGCCGACCCTGAGTGCAGTGAGGTTGGC 1938
      ||||||||||||||||||||||||||||||||||||||||||||||||||
1951  TGTGACGGGCCAGGACCAGACCACTGCAATGACTGTTTGCACTACTACTA 2000
      ||||||||||||||||||||||||||||||||||||||||||||||||||
```

FIG. 11H

```
1939  TGTGACGGGCCAGGACCAGAGACCACTGCAATGACTGTTTGCACTACTACTA  1988
          ||||||||||||||||||||||||||||||||||||||||||||||||||
2001  CAAGCTGAAAAACAATACCAGGATCTGTGTCTCCAGCTGCCCCCCTGGCC    2050
          ||||||||||||||||||||||||||||||||||||||||||||||||
1989  CAAGCTGAAAAACAATACCAGGATCTGTGTCTCCAGCTGCCCCCCTGGCC    2038

2051  ACTACCACGCCGACAAGAAGCGCTGCAGGAAGTGTGCCCCAACTGTGAG     2100
          |||||||||||||||||||||||||||||||||||||||||||||||
2039  ACTACCACGCCGACAAGAAGCGCTGCAGGAAGTGTGCCCCAACTGTGAG     2088

2101  TCCTGCTTTGGGAGCCATGGTGACCAATGCCATGTCCTGCAAATATGGATA   2150
          ||||||||||||||||||||||||||||||||||||||||||||||||||
2089  TCCTGCTTTGGGAGCCATGGTGACCAATGCCATGTCCTGCAAATATGGATA   2138

2151  CTTTCTGAATGAAGAACCAACAGCTGTGTTACTCACTGCCCTGATGGGT    2200
          ||||||||||||||||||||||||||||||||||||||||||||||||
2139  CTTTCTGAATGAAGAACCAACAGCTGTGTTACTCACTGCCCTGATGGGT    2188

2201  CATATCAGGATACCAAGAAAAATCTTTGCCGGAAATGCAGTGAAAACTGC   2250
          ||||||||||||||||||||||||||||||||||||||||||||||||||
```

FIG. 11I

```
2189 CATATCAGGATATACCAAGAGAAAAATCTTTGCCGGAAATGCAGTGAAAACTGC 2238
           ||||||||||||||||||||||||||||||||||||||||||||||||||
2251 AAGACATGTACTGAATTCCATAACTGTACAGAATGTAGGGATGGGTTAAG 2300
     ||||||||||||||||||||||||||||||||||||||||||||||||||
2239 AAGACATGTACTGAATTCCATAACTGTACAGAATGTAGGGATGGGTTAAG 2288
           ||||||||||||||||||||||||||||||||||||||||||||||||||
2301 CCTGCAGGGATCCCGGTGCTCTGTCTCCTGTGAAGATGGACGGTATTTCA 2350
     ||||||||||||||||||||||||||||||||||||||||||||||||||
2289 CCTGCAGGGATCCCGGTGCTCTGTCTCCTGTGAAGATGGACGGTATTTCA 2338
           ||||||||||||||||||||||||||||||||||||||||||||||||||
2351 ACGGCCAGGACTGCCAGCCCACTGTTCTGCCACCGCTTCTGCCACTTGTGCTGGG 2400
     ||||||||||||||||||||||||||||||||||||||||||||||||||
2339 ACGGCCAGGACTGCCAGCCCACTGTTCTGCCACCGCTTCTGCCACTTGTGCTGGG 2388
           ||||||||||||||||||||||||||||||||||||||||||||||||||
2401 GCAGGAGCTGATGGGTGCATTAACTGCACAGAGGGCTACTTCATGGAGGA 2450
     ||||||||||||||||||||||||||||||||||||||||||||||||||
2389 GCAGGAGCTGATGGGTGCATTAACTGCACAGAGGGCTACTTCATGGAGGA 2438
           ||||||||||||||||||||||||||||||||||||||||||||||||||
2451 TGGGAGATGCGTGCAGAGCTGTAGTATCAGCTATTACTTTGACCACTCTT 2500
     ||||||||||||||||||||||||||||||||||||||||||||||||||
```

FIG-11J

```
2439  TGGGAGATGCGTGCAGAGCTGTAGTATCAGCTATTACTTTGACCACTCTT  2488
      |||||||||||||||||||||||||||||||||||||||||||||||||
2501  CAGAGAATGGATACAAATCCTGCAAAAATGTGATATCAGTTGTTTGACG  2550
      ||||||||||||||||||||||||||||||||||||||||||||||||
2489  CAGAGAATGGATACAAATCCTGCAAAAATGTGATATCAGTTGTTTGACG  2538

2551  TGCAATGGCCCAGGATTCAAGAACTGTACAAGCTGCCCTAGTGGGTATCT  2600
      |||||||||||||||||||||||||||||||||||||||||||||||||
2539  TGCAATGGCCCAGGATTCAAGAACTGTACAAGCTGCCCTAGTGGGTATCT  2588

2601  CTTAGACTTAGGAATGTGTCAAATGGGAGCCATTTGCAAGGATGCAACGG  2650
      |||||||||||||||||||||||||||||||||||||||||||||||||
2589  CTTAGACTTAGGAATGTGTCAAATGGGAGCCATTTGCAAGGATGCAACGG  2638

2651  AAGAGTCCTGGGCGGAAGGAGGCTTCTGTATGCTTGTGAAAAAGAACAAT  2700
      |||||||||||||||||||||||||||||||||||||||||||||||||
2639  AAGAGTCCTGGGCGGAAGGAGGCTTCTGTATGCTTGTGAAAAAGAACAAT  2688

2701  CTGTGCCAACGGAAGGTTCTTCAACAACTTTGCTGCAAAACATGTACATT  2750
      |||||||||||||||||||||||||||||||||||||||||||||||||
```

FIG-11K

```
2689  CTGTGCCAACGGAAGGTTCTTCAACAACTTTGCTGCAAAACATGTACATT  2738
2751  CCAAGGCTGAGCAGCC..................................  2766
      ||||||||||||||||
2739  TCAAGGCTGAGCAGCCATCTTAGATTTCTTTGTTCCTGTAGACTTATAGA  2788
```

FIG. 11L

```
Miranda1                                                        .                                                  50
         1  MDWDWGNRCSRPGRRDLLCVLALLAGCLLPVCRTRVYTNHWAVKIAGGFA
            ||||||||||||||||||||||||||||||||||||||||||||||||:
IRCM     1  MDWDWGNRCSRPGRRDLLCVLALLGGCLLPVCRTRVYTNHWAVKIAGGFP   50

.                     100
        51  EADRIASKYGFINVGQIGALKDYYHFYHSRTIKRSVLSSRGTHSFISMEP
            ||||||||||||||:||||||||||||||||||||||:|||||||||||
        51  EANRIASKYGFINIGQIGALKDYYHFYHSRTIKRSVISSRGTHSFISMEP   100

.                     150
       101  KVEWIQQQVVKKRTKRDYDLSHAQSTYFNDPKWPSMWYMHCSDNTHPCQS
            ||||||||||||||||||:||:|||||||||||||||||||||||||||
       101  KVEWIQQQVVKKRTKRDYDFSRAQSTYFNDPKWPSMWYMHCSDNTHPCQS   150

.                     200
       151  DMNIEGAWKRGYTGKNIVVTILDDGIERTHPDLMQNYDALASCDVNGNDL
            ||||||||||||||||||||||||||||||||||||||||||||||||||
       151  DMNIEGAWKRGYTGKNIVVTILDDGIERTHPDLMQNYDALASCDVNGNDL   200

.                     250
       201  DPMPRYDASNENKHGTRCAGEVAAAANNSHCTVGIAFNAKIGGVRMLDGD
            ||||||||||||||||||||||||||||||||||||||||||||||||||
       201  DPMPRYDASNENKHGTRCAGEVAAAANNSHCTVGIAFNAKIGGVRMLDGD   250
```

FIG. 12A

```
251  VTDMVEAKSVSFNPQHVHIYSASWGPDDDGKTVDGPAPLTRQAFENGVRM  300
     |||||||||||||||||||||||||||||||||||||||||||||||||
251  VTDMVEAKSVSFNPQHVHIYSASWGPDDDGKTVDGPAPLTRQAFENGVRM  300

301  GRRGLGSVFVWASGNGGRSKDHCSCDGYTNSIYTISISSTAESGKKPWYL  350
     |||||||||||||||||||||||||||||||||||||||||||||||||
301  GRRGLGSVFVWASGNGGRSKDHCSCDGYTNSIYTISISSTAESGKKPWYL  350

351  EECSSTLATTYSSGESYDKKIITTDLRQRCTDNHTGTSASAPMAAGIIAL  400
     |||||||||||||||||||||||||||||||||||||||||||||||||
351  EECSSTLATTYSSGESYDKKIITTDLRQRCTDNHTGTSASAPMAAGIIAL  400

401  ALEANPFLTWRDVQHVIVRTSRAGHLNANDWKTNAAGFKVSHLYGFGLMD  450
     |||||||||||||||||||||||||||||||||||||||||||||||||
401  ALEANPFLTWRDVQHVIVRTSRAGHLNANDWKTNAAGFKVSHLYGFGLMD  450

451  AEAMVMEAEKWTTVPRQHVCVESTDRQIKTIRPNSAVRSIYKASGCSDNP  500
     |||||||||||||||||||||||||||||||||||||||||||||||||
451  AEAMVMEAEKWTTVPRQHVCVESTDRQIKTIRPNSAVRSIYKASGCSDNP  500
```

FIG. 12B

```
501  NRHVNYLEHVVVRITITHPRRGDLAIYLTSPSGTRSQLLANRLFDHSMEG    550
     |||||||||||||||||||||||||||||||||||||||||||||||||
501  NRHVNYLEHVVVRITITHPRRGDLAIYLTSPSGTRSQLLANRLFDHSMEG    550

551  FKNWEFMTIHCWGERAAGDWVLEVYDTPSQLRNFKTPGKLKEWSLVLYGT    600
     |||||||||||||||||||||||||||||||||||||||||||||||||
551  FKNWEFMTIHCWGERAAGDWVLEVYDTPSQLRNFKTPGKLKEWSLVLYGT    600

601  SVRPYSPTNEFPKVERFRYSRVEDPTDDYGTEDYAGPCDPECSEVGCDGP    650
     ||·|||||||||||||||||||||||||||||||||||||||||||||||
601  SVQPYSPTNEFPKVERFRYSRVEDPTDDYGTEDYAGPCDPECSEVGCDGP    650

651  GPDHCNDCLHYYYKLKNNTRICVSSCPPGHYHADKKRCRKCAPNCESCFG    700
     |||||||||||||||||||||||||||||||||||||||||||||||||
651  GPDHCNDCLHYYYKLKNNTRICVSSCPPGHYHADKKRCRKCAPNCESCFG    700

701  SHGDQCMSCKYGYFLNEETNSCVTHCPDGSYQDTKKNLCRKCSENCKTCT    750
     |||||||||||||||||||||||||||||||||||||||||||||||||
701  SHGDQCMSCKYGYFLNEETNSCVTHCPDGSYQDTKKNLCRKCSENCKTCT    750
```

FIG-12C

```
751  EFHNCTECRDGLSLQGSRCSVSCEDGRYFNGQDCQPCHRFCATCAGAGAD  800
     ||||||||||||||||||||||||||||||||||||||||||||||||||
751  EFHNCTECRDGLSLQGSRCSVSCEDGRYFNGQDCQPCHRFCATCAGAGAD  800

801  GCINCTEGYFMEDGRCVQSCSISYYFDHSSENGYKSCKKCDISCLTCNGP  850
     ||||||||||||||||||||||||||||||||||||||||||||||||||
801  GCINCTEGYFMEDGRCVQSCSISYYFDHSSENGYKSCKKCDISCLTCNGP  850

851  GFKNCTSCPSGYLLDLGMCQMGAICKDATEESWAEGGFCMLVKKNNLCQR  900
     ||||||||||||||||||||||||||||||||||||||||||||||||||
851  GFKNCTSCPSGYLLDLGMCQMGAICKDATEESWAEGGFCMLVKKNNLCQR  900

901  KVLQQLCCKTCTFQG.   915
     |||||||||||||||
901  KVLQQLCCKTCTFQG*   916
```

FIG-12D

PRO-PROTEIN CONVERTING ENZYME

This is a national stage application of PCT/CA97/00535 which claims the benefit of provisional application No. 60/021,008, filed Jul. 26, 1996.

FIELD OF THE INVENTION

This invention relates to protein processing enzymes or pro-hormone convertases (PCs), specifically to PC5, more specifically to the human PC5.

BACKGROUND OF THE INVENTION

Pro-hormone convertases (PCs) belong to a family of enzymes responsible for the maturation of proteic precursors into active proteins or enzymes. Up to now, many human enzymes of that family have been identified, namely furin, PC1, PC2, PC4 and PC7. Each enzyme has a tissular distribution which may be restricted (for example, PC4 is restricted to male germ cells) or ubiquitous (furin is such an example). Although all these enzymes share the properties of cleaving precursor proteins at basic or dibasic residues, they nevertheless have differing cleavage specificities. The action of a specific pro-hormone convertase is therefore governed by the cleavage sequence of a given protein substrate, and/or by the location of that enzyme in a tissue expressing or responding to a given proteic substrate growth factor or hormone.

Renin is an aspartyl protease which makes an important contribution to cardiovascular physiology and pathophysiology through its key role in the synthesis of the vasoactive octapeptide angiotensin II (AII). While the kidney is the primary source of circulating active renin, several additional tissues, including the pituitary and adrenal glands, placenta, uterus, ovary, testes, heart, vasculature and brain express the renin gene (reviewed in [1-4]). The presence of additional components of the RAS (renin-angiotensin system) in these tissues, including angiotensin converting enzyme (ACE) and angiotensin II receptors, has led to the proposal that certain tissues might contain a locally active tissue renin-angiotensin system (tRAS) although the actual function of the various tRAS is still largely a matter of conjecture.

Renin is first synthesized as an enzymatically inactive precursor, prorenin, which is converted to active renin by the proteolytic removal of a 43 amino acid amino-terminal prosegment. The activity of the RAS within any given tissue would, therefore, be dependent on the existence of proteolytic enzymes capable of converting prorenin to active renin and on the expression of such prorenin processing enzymes (PPEs) in the same cells that express prorenin. The identity of the enzyme(s) responsible for the proteolytic activating human prorenin in vivo is still uncertain. Furthermore, it is possible that multiple PPEs exist in humans and these may differ among renin-producing tissues. Biochemical and microscopic studies of renin in the kidney suggest that candidate PPEs should be selective for cleavage of human prorenin at $Lys^{42}$, $Arg^{43}$ of the prosegment[5] and would be active in secretory granules of the juxtaglomerular (JG) cells.[6] The lysosomal enzyme cathepsin B has been co-localized with human renin/prorenin in the secretory granules of JG cells and human pituitary lactotrophs[7,8] and has been shown to cleave human prorenin in vitro with a high affinity and selectivity for the proper cleavage site.[9] The prohormone convertase PC1 has also been shown to cleave human prorenin with the correct site- and organelle specificity in transfected cells[10] and to co-localize with renin in the adrenal medulla and derived tumors[11], but not in JG cells.[12]

In an effort to identify novel PPEs, we recently determined the distribution of processing enzymes in an established renin-expressing tissue culture cell line derived from an oncogene-induced mouse tumor (As4.1 cells[13]). One such enzyme, the mouse prohormone convertase PC5, was found. Mouse PC5 is capable of partially cleaving human prorenin.

Miranda et al. (38) describe the cDNA and protein sequences for a human PC6 enzyme obtained by PCR from $CD4^+$ T lymphocytes. PC5 and PC6 are different names given to what appears to be the same enzyme. However, the sequences of Miranda et al. comprise a plurality of substitutions when compared to the present PC5 sequences. Moreover, the size of messenger RNA encoding PC6 and PC5 are similar but not identical. Since the present PC5 sequences were obtained from human adrenals, both enzymes may be isoforms, differentially expressed in tissues and they may have different activities.

Prorenin and HIV gp160 are most probably not the only proteic precursors to be recognized and cleaved by PC5. Many growth factors responsible for cell proliferation are cleaved by one or more PCs: they include platelet-derived-growth factors A and B (PDGF's), epidermal-growth-factor (EGF), insulin-like growth factors I and II (IGF's), transforming growth factors α and β (TGF's). Each of these named growth factors has the typical cleavage site motif $K/R-(X)_n-R\downarrow$ (where n=0,2,4,6). Full biological potency is conferred to these growth factors only after cleavage at these sites, by one or more of the PC enzyme family. There is therefore a possibility that manipulating the expression of the PCs would affect cell proliferation via deficient growth factor activation.

Out of the >450,000 patients/year in the U.S. and Canada who undergo percutaneous transluminal coronary angioplasty (PTCA), 30–50% of them will restenose their coronaries within 3–6 months. This flare-up of endothelial and smooth-muscle cells proliferation is due to the activation of numerous regulatory growth factors. Therefore, knowing which enzyme(s) is (are) responsible for this activation, and manipulating the level of expression of this or theses enzyme(s) would be particularly useful to prevent restenosis.

STATEMENT OF THE INVENTION

The present invention relates to the human PC5 (hPC5). We demonstrate that hPC5 isolated form human adrenals proteolytically activates human prorenin with the expected site- and organelle- specificity and that it is co-expressed with prorenin in the zona glomerulosa of the adrenal cortex. Therefore, PC5 is a prorenin-processing enzyme (PPE). Silencing the expression of PC5 would find a specific application in inhibiting the production of renin, and a method of inhibiting the production of renin is an object of the invention. Since the production of renin is one of targets of the RAS involved in hypertension. Furthermore, we demonstrate that hPC5 is overexpressed in atherosclerotic coronary arteries. Antisense oligonucleotides have been designed, amongst which one has been shown to successfully silence the expression of hPC5 in smooth muscle cells in culture. This antisense inhibited carotid stenosis in a in vivo rabbit carotid injury model. These results indicate that a method of silencing the expression of PC5 would find a specific application in preventing restenosis.

PC5 is known to be expressed in $CD4^+$ T cells, along with furin and PC7. The three enzymes are capable of converting HIV gp160 into its fusiogenic form. Therefore, antisense constructs, particularly the oligonucleotide that successfully inhibited restenosis, will find a use in inhibiting expression of the activity of PC5 towards HIV gp160.

The complete amino acid and nucleotide sequence of hPC5 is described hereinbelow and are another object of this invention. Recombinant vectors and hosts comprising as a new insert, whole or part of hPC5, are also an object of the invention.

Oligopeptides derived from the proteic sequence of hPC5 are also an object of the invention.

Antibodies directed against the whole protein hPC5 or a part thereof are also an object of the invention.

Diagnostic methods and kits comprising oligonucleotides or antibodies binding PC5 nucleic acids or protein or peptides are also an object of the invention.

This invention will be described hereinbelow by way of specific embodiments, examples and figures which purpose is to illustrate the contemplated aspects of the invention, and not to limit the scope of the invention.

BRIEF DESCRIPTION OF THE DRAWINGS

FIG. 1: Schematic diagram of the isolated cDNAs encoding HPC5. Restriction enzyme sites used in sub-cloning are denoted. Solid lines represent clones isolated from a phage library. Hatched lines denote the portion of the cDNA isolated by RT-PCR of human adrenal mRNA. The double line represents the portion of the mouse PC5 CDNA (corresponding to the amino terminus of the signal peptide) which was used to complete the cDNA for expression.

FIGS. 2A–2B: Nucleotide and derived protein sequence of hPC5 (SEQ ID NOS: 1 and 2, respectively). Proposed signal peptide (solid arrow) and prosegment (open arrow) cleavage sites are denoted based on data from mouse PC5.[15] The underlined sequence represents the portion of the signal peptide from mouse PC5 which was used in the expression vector construction.

FIG. 3: Distribution on PC5 RNA in various human tissues.

Each lane contains 2 $\mu$g poly-A RNA. Filters were hybridized with a radiolabeled probe for hPC5 as described in Materials and Methods. Shown at left is the migration of single strand size standards in kilobases (Kb). Note that the absolute is signal cannot be compared between the two filters as they were of different ages and hybridized at different times.

Figure 4B:
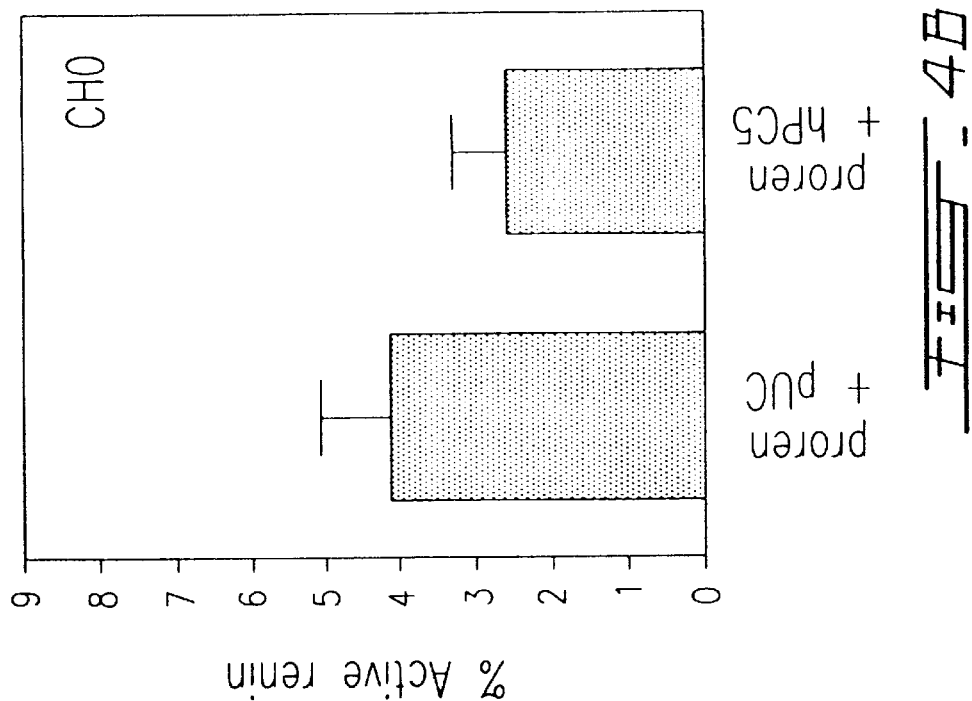
Figure 4A:
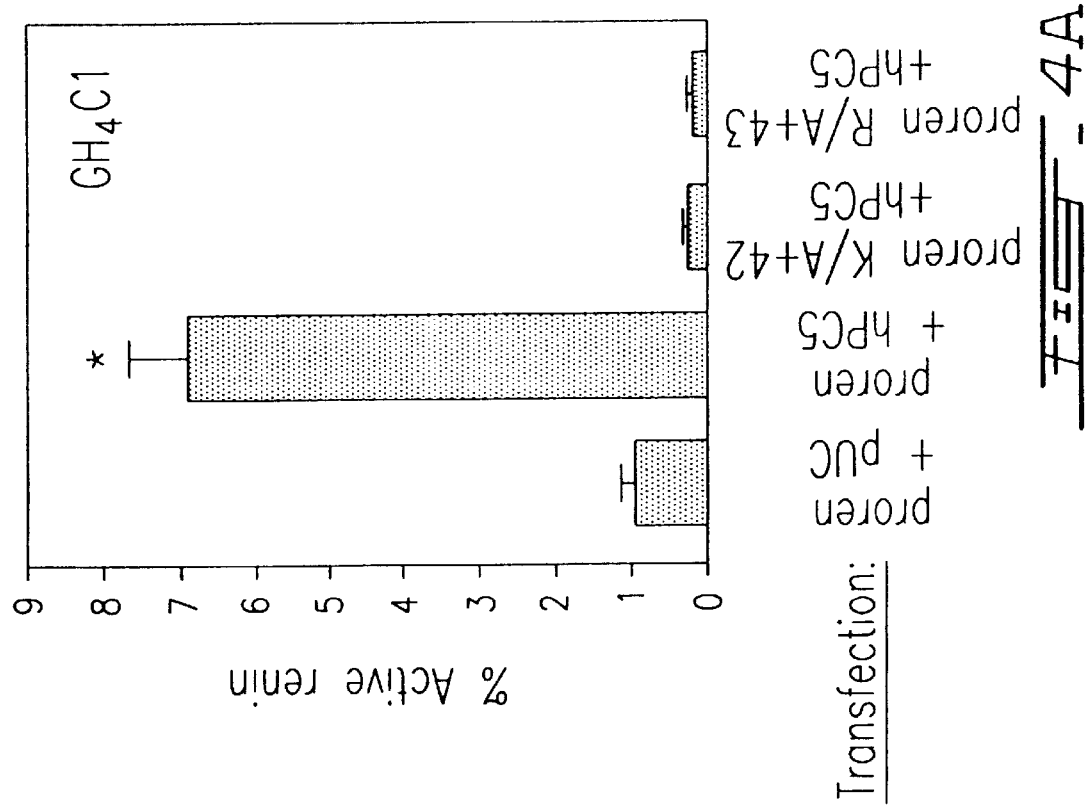

FIGS. 4A–4B: hPC5 cleaves human prorenin with site and cell specificity. Panel A: $GH_4C_1$ cell were co-transfected with expression vectors for the indicated proteins. Supernatants were collected 30 hrs. after transfection and assayed for % active renin [(active renin/total renin)×100]. Bars represent the mean±S.E.M of 9 independent transfections. *=P<0.0001 as compared to proren+pUC, as determined by the Mann-Whitney non-parametric test. Panel B: Resulting secretion of active renin after co-transfection of CHO cells with an expression vector for prorenin and either a control plasmid (pUC) or hPC5.Bars represent the mean±S.E.M of 3 independent transfections.

Figure 5:
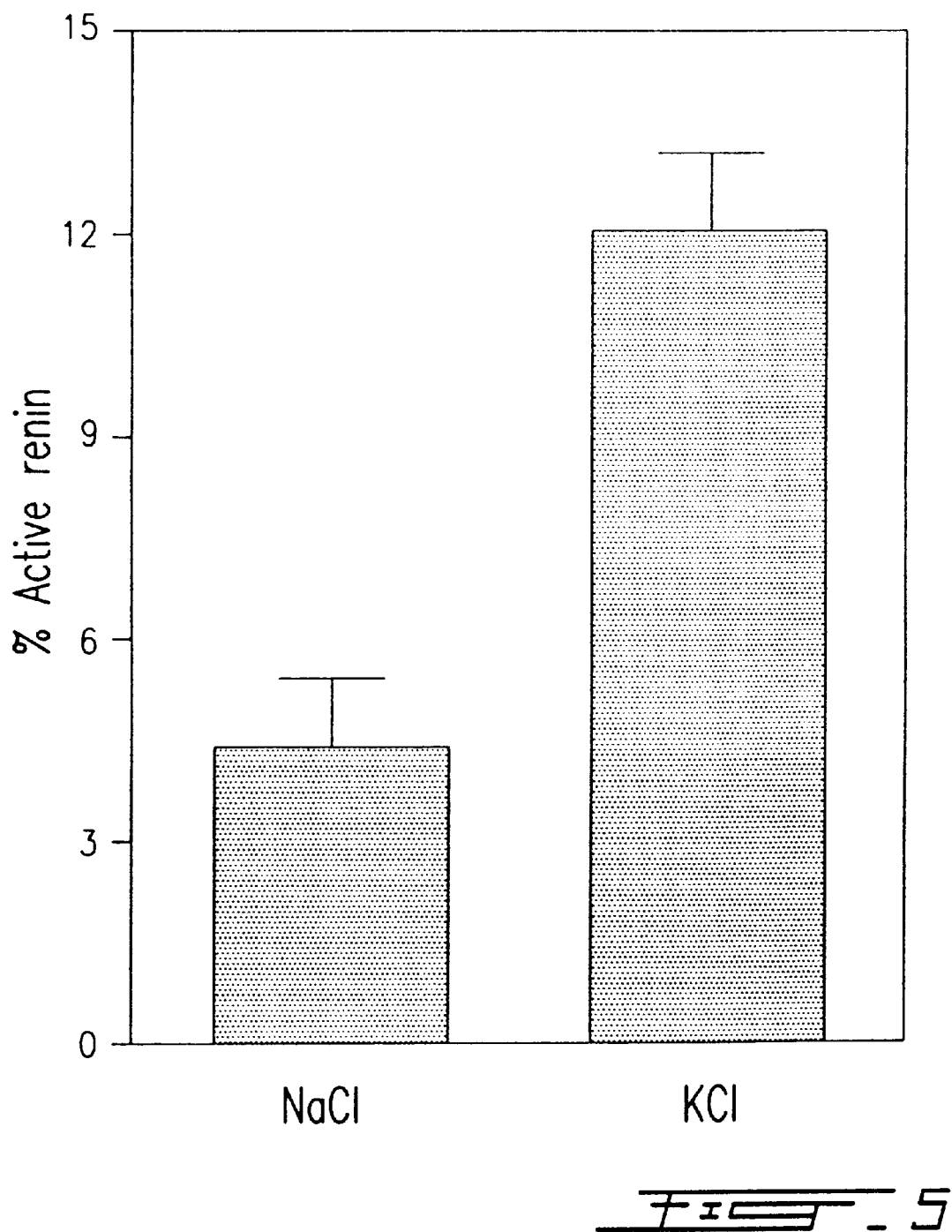

FIG. 5: Active renin generation in secretory granules of co-transfected $GH_4C_1$ cells. Parallel wells of $GH_4Cl$ cells co-transfected with expression vectors for human prorenin and human PC5 were incubated for 20 min. in medium containing either 50 mmol/L NaCl (control) or 50 mmol/L KCl (a de-polarizing agent which causes the acute release of secretory granules). Percent active renin was calculated as described in the legend to FIG. 4A. Bars represent the mean±SEM of 3 independent transfections. *=P<0.005 using Student's t-test.

Figure 6:
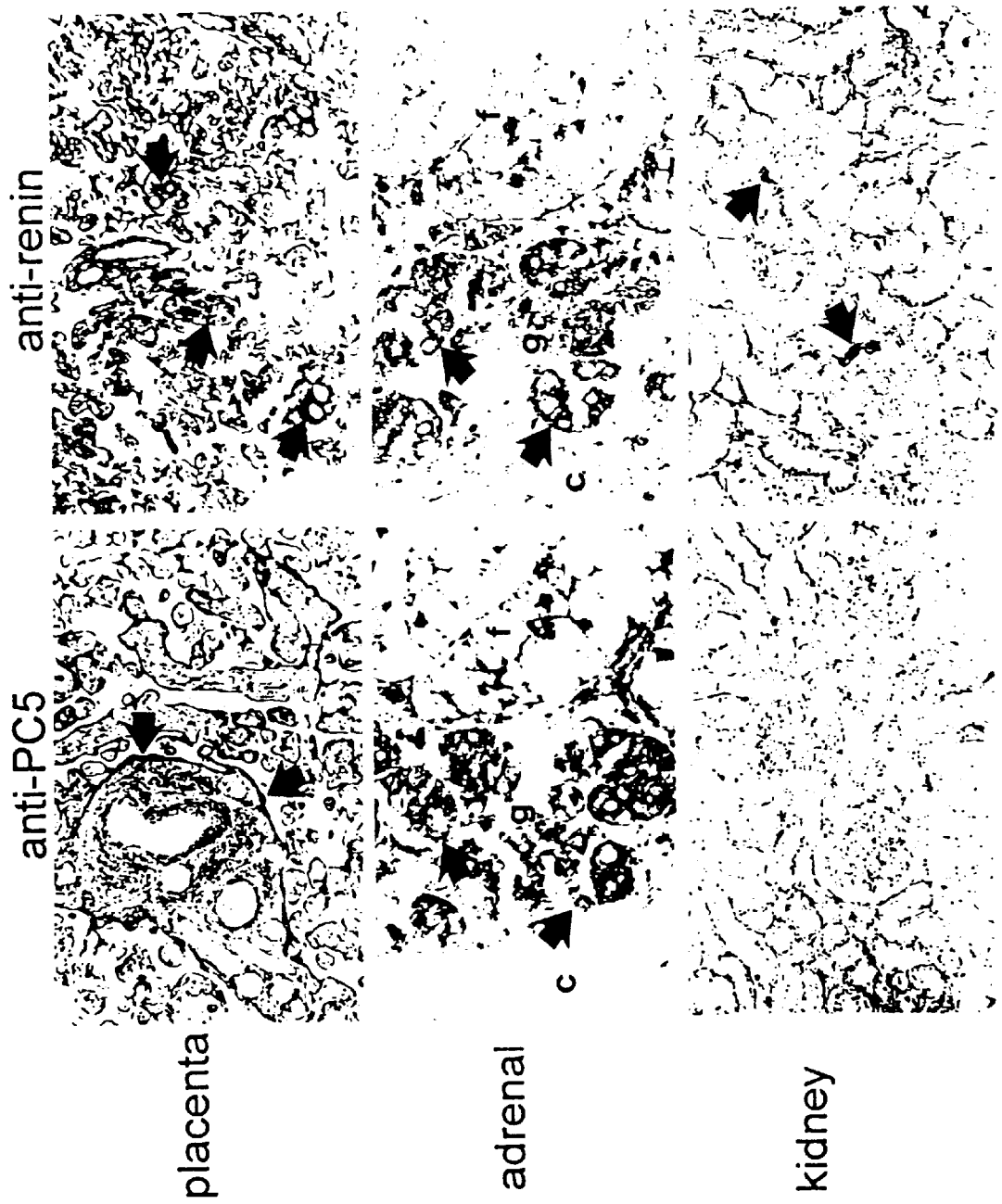

FIG. 6: Immunodetection of hPC5 and renin/prorenin in renal cortex, human placental cotyledon and adrenal gland. Positively stained areas are denoted by solid arrows. Sections in adrenal cortex are separated by 5 mM to show co-localization in the cells of the zona glomerulosa (g) and absence of staining in the capsule (c) and zona fasciculata (f). Original magnification 25× (kidney and placenta) and 80× (adrenal gland).

Figure 7:
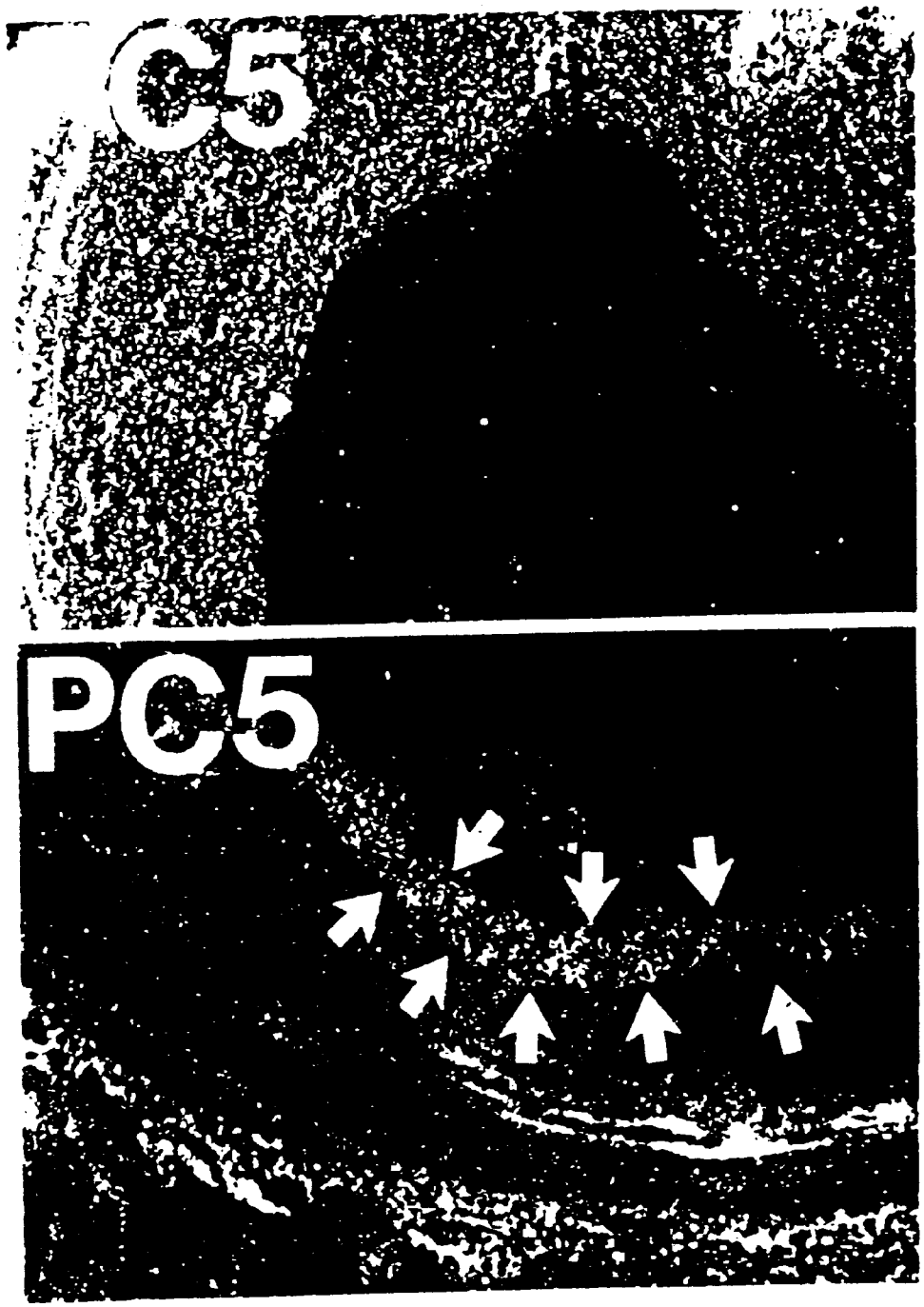

FIG. 7: In vivo hybridization analysis of PC5 mRNA in human coronary blood vessels in atherosclerosis. The lower panel show a vessel where a severe lesion was observed. PC5 MRNA was abundantly expressed in this vessel, in the smooth muscle cells in the neointimal formation (see arrows). In comparison, another vessel which is free of any lesion, did not express PC5 mRNA (shown in the upper panel).

Figure 8:
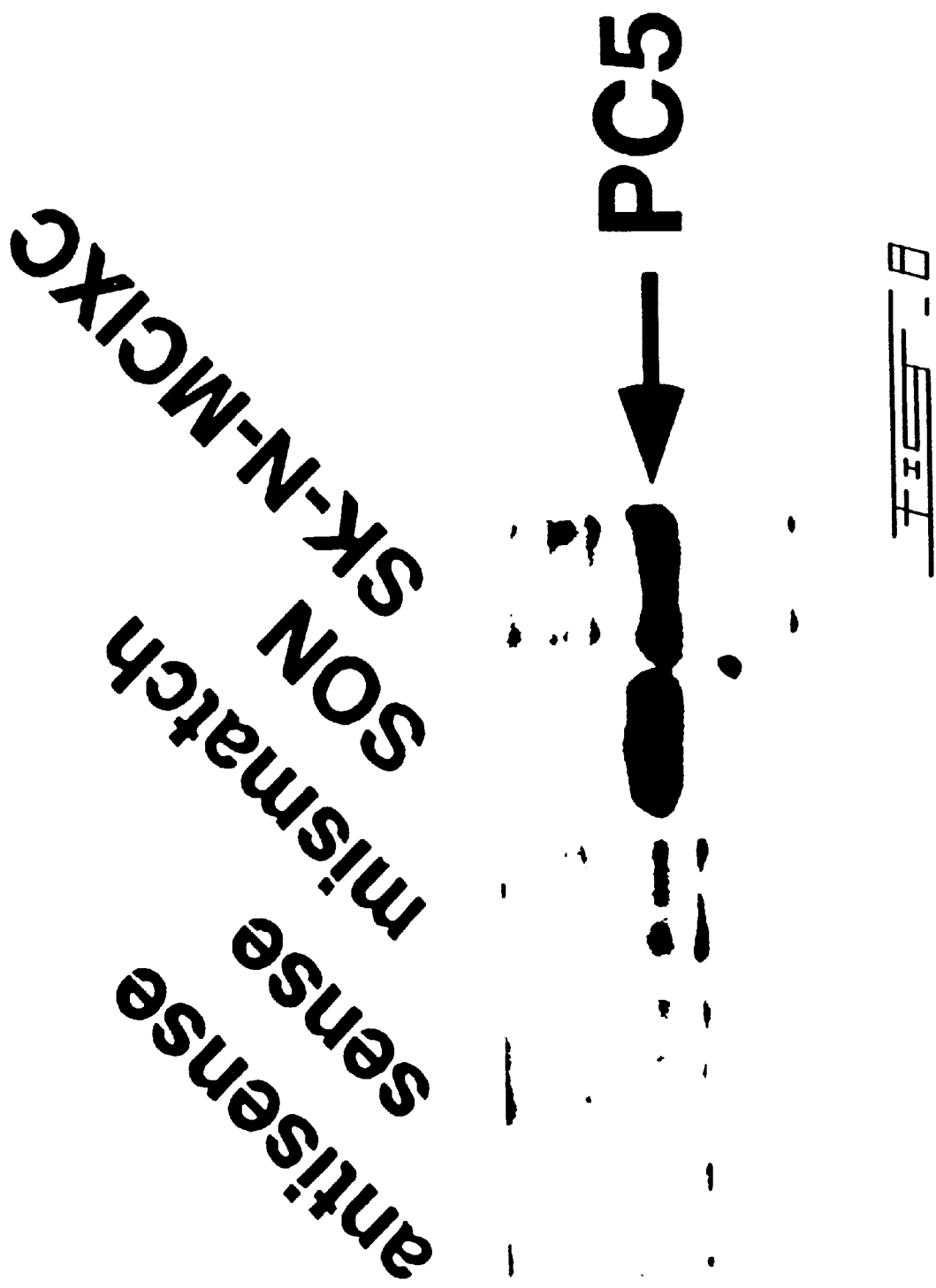

FIG. 8: Western blot analysis of PC5 protein in rabbit smooth muscle cells treated with either antisense, sense or mismatch PC5 oligonucleotides. The specific PC5 band is identified (see arrow) by comparison with proteins extracted from rat supraoptic nucleus (SON) and SK-N-MCIXC cells (human neuroepithelioma). In the sample extracted from antisense PC5 treatment, we observe a dramatic decrease in the level of PC5 signal (approximately 2–3 fold decrease) in comparison to the control sense or mismatch PC5 oligos. This indicates that the antisense treatment reduced significantly the protein levels of PC5 in rabbit smooth muscle cells.

FIG. 9: Rabbit in vivo test of the PC5 antisense ODN as compared to the control sense and random ODNs. It shows a decreased stenosis due to the presence of a PC5 antisense when compared to the sense and random controls.

FIG. 10: Proprotein convertase immunoreactivity in human atherectomy specimens. It shows the presence of the enzymes of the pro-hormone convertase family which are present in the specimens.

FIG. 11: Illustrates differences between cDNA sequences of PC6 (Miranda et al. SEQ ID No. 6) and PC5 (present invention).

FIG. 12: Illustrates differences between protein sequences of PC6 (Miranda et al. SEQ ID No. 7) and PC5 (present invention).

DESCRIPTION OF THE INVENTION

Materials and Methods cDNA library construction and screening: A cDNA library derived from total human adrenal RNA was constructed by Stratagene (La Jolla, Calif.) in the phage vector Uni-Zap XR. Six hundred thousand phage plaques were screened initially using radioactive probes and standard methodologies.[14] The initial hybridization probe was a 320 base pair DNA fragment derived from reverse-transcriptase PCR of human brain RNA using information derived from an unidentified human CDNA sequence tag in Genbank (Accession # M85522) with a high degree of similarity to the previously cloned mouse PCS.[15] Fragment labeling was carried out using $^{32}p$ dCTP and a random primer labeling kit (Boehringer-Mannheim Canada, Laval, Quebec, Canada) according to manufacturer's instructions. One positive hybridizing phage (hPC5A) was identified. Its insert was sequenced in its entirety using the dideoxy-chain termination method and found to code for an 1150 base pair CDNA with a high degree of sequence similarity to mouse PCS (data not shown). A 1070 base pair fragment (excluding the poly A tail) was excised from hPC5A, labeled and used to re-screen an additional 600,000 phage from the CDNA library. A second phage clone (hPC5B) was isolated and found to contain an 1807 base pair cDNA insert overlapping hPC5A and extending toward the 5' end of the cDNA (FIG. 1).

Reverse-transcriptase PCR: One microgram of poly A+ RNA from total human adrenal (Clontech Laboratories, Palo Alto, Calif.) was subjected to reverse transcriptase polymerase chain reaction (RT-PCR) using a published procedure[16] and the following oligonucleotides:
Forward oligonucleotide; derived from a region corresponding to the signal peptide of mouse PC5.[15] An artificial HindIII restriction enzyme cleavage site added to the 5'-end of the amplified fragment for the purpose of cloning is underlined:

5'-CCAAGCTTGGCTGCTGTGCGTGCTGGC-3' (SEQ ID No 8)

Reverse oligonucleotide; derived from the 5'-end of the phage hPC5B. An internal BglII restriction enzyme site is underlined:

5'-CTGCCTTCAGATCTGTAGTG-3' (SEQ ID No 9)

The entire RT-PCR reaction was repeated 4 times and 4 independently derived clones of the amplified fragment were sequenced and the sequences were compared. The sequence submitted to Genbank (Accession #U49114) represents the consensus sequence, defined as any nucleotide appearing in ¾ clones.

Northern blot analysis: Tissue distribution of PC5 MRNA was determined by hybridizing commercially purchased nitrocellulose filters containing aliquots (2 μg) of Poly-A RNA from various human tissues (Clontech Laboratories, Palo Alto, Calif.). The probe used was a complementary RNA derived from the full length hPC5 CDNA. Probe labeling and hybridization were carried out as previously described.[17]

Expression vector construction: A cDNA fragment from the KpnI site (FIG. 1) to just past the stop codon was excised from the phage hPC5B and combined with a KpnI to HindIII (see above) fragment derived from portions of two independent RT-PCR clones (so as to eliminate errors arising from the Taq polymerase). A region corresponding to the first 16 amino acids of the signal peptide derived from mPC5 was attached to the 5'-end by overlap-extension PCR.[18] Thus, the entire CDNA, encoding amino acids 1–16 derived from the mPC5 signal peptide and the remainder from hPC5, was subcloned into the expression vector RSV-globin[19] which places the cDNA under the control of the RSV promoter and provides a 3' intron and polyadenylation signal from the rabbit beta globin gene. The entire subcloned fragment was subsequently verified by DNA sequencing.

Cell culture and transfection: GH$_4$C1 cells were plated in 6-well culture dishes at a density of 5×10$^5$ cells per well. Twenty four hours later, medium was changed and the cells were transfected by the DEAE-dextran method using a commercial kit (CellPhect Transfection kit, Pharmacia Biotech, Baie D'urfe, Quebec, Canada) according to manufacturer's instructions. Each well received 0.18 μg of either the hPC5 expression vector or a neutral plasmid vector (pUC18) and 0.18 μg of an expression vector for human prorenin (pRHR1100) or its equivalents in which amino acids 42 or 43 of the prorenin prosegment were mutated to alanine (K/A-2 and R/A-1, respectively[20]). Supernatants were collected 30 hrs. after transfection and assayed for prorenin and renin content as previously described.[20]

To verify that conversion of the prorenin occurred in the secretory granules, GH$_4$C1 transfected with the human prorenin and hPC5 expression vectors were stimulated to release secretory granules by depolarization using a previously published technique.[21] Forty hrs. after co-transfection, the culture medium in parallel wells of transfected cells was replaced with pre-warmed medium supplemented to a final concentration of 50 mmol/L with either NaCl (control) or KCl (secretagogue). The media were collected after 20 min. and assayed for renin/prorenin. A potassium-dependent increase in the percent active renin contained in cell supernatants was taken as an indication of active renin release from the secretory granules of the transfected cells. Results shown in FIG. 5 represent the mean of three independent transfection experiments.

Immunolocalization of hPC5 in human tissues: Human tissue was obtained post-mortem (kidney and adrenal gland) or post-partum (placental cotyledon), fixed in Bouin's solution and embedded in paraffin. For immunolocalization, 5 μm sections were mounted on gelatin-coated slides, deparaffinized and incubated with a 1:50 dilution of a polyclonal rabbit antiserum raised against a peptide corresponding to the N-terminal 16 amino acids of rat PC5 (PC5.MAP antibody) or a 1:200 dilution of a polyclonal rabbit antiserum against recombinant human prorenin. For kidney and placental specimens, immune complexes were revealed by incubation with protein A-colloidal gold (15 nm particles) synthesized from tetra-chloroauric acid (BDH) according to the method of Ghitescu and Bendayan.[22] Gold particles were enhanced for viewing in the light microscope by incubation with silver (IntenSE ™M Silver Enhancement Kit, Amersham Life Science, Oakville, Ontario, Canada) and sections were counter-stained with hematoxylin and methyl green. Immune complexes on human adrenal sections were detected with a 1:200 dilution of biotin-labeled donkey anti-rabbit IgG and a 1:300 dilution of streptavidin-horseradish peroxidase complex (Amersham Life Science, Oakville, Ontario, Canada) and were incubated with diaminobenzidine and hydrogen peroxide (Sigma Chemicals, St. Louis, Mo.) as chromogen. All positive staining patterns were subsequently verified for specificity by omission of the first antibody.

RESULTS

The primary sequence of human PC5 is shown in FIG. 2. We were unable to clone the extreme 5'-end of the CDNA either by the RACE protocol[16] or by using oligonucleotides based on the published sequence of mouse PC5[15,23], possibly due to a high G/C content of the cDNA in this region. However, based on the published cDNA sequences for rat and mouse PC5[15], we are confident that we have isolated all but the 5'-most portion of the CDNA corresponding to the first 12 amino acids of the signal peptide. By comparison with the published sequence of mouse PC5, we predict that the cDNA isolated would code for a preproPC5 of 915 amino acids, including a signal peptide and a prosegment of 32 and 84 amino acids, respectively. The deduced sequence of hPC5 is 88% identical to the previously published mouse PC5 cDNA and 96% identical to the mouse PC5 protein.

Northern analysis of poly A RNA from a variety of human tissues reveals a major band of approximately 6.6 Kb and a minor band at approximately 3.8 Kb (FIG. 3). PC5 RNA is detected in the brain, heart, placenta, lung, thyroid gland and testes and at lower levels in the skeletal muscle, kidney and pancreas, small intestine and stomach. In the adrenal gland, PC5 is particularly enriched in the cortex (FIG. 3).

Because PC5 RNA appears to be expressed in a number of tissues previously reported to contain active renin, we have tested the ability of hPC5 to cleave human prorenin in a cell co-transfection assay (FIG. 4A). As has been previously reported[10], when cultured rat sommatotrophic $GH_4C1$ cells are co-transfected with an expression vector encoding human prorenin and a neutral plasmid vector, only unprocessed prorenin is secreted into the culture supernatant. In contrast, if the human prorenin expression vector is co-transfected with an expression vector encoding human PC5, a portion of the expressed prorenin is secreted as active renin. Co-expression of human PC5 with prorenin mutated at either of the basic residues forming the native cleavage site (Lysine 42 or Arginine 43) prevents activation. These results suggest that human PC5 activates human prorenin by proteolytic cleavage at the site previously reported for activation of renin in humans.[5] While human PC5 cleaves human prorenin in $GH_4C1$ cells, there is no apparent increase in active renin secretion when co-transfections are carried out in Chinese Hamster Ovary (CHO) cells (FIG. 4B). One obvious difference in the CHO cell line as compared to $GH_4C1$ cells is their lack of secretory granules, suggesting that either human PC5 or human prorenin or both require the secretory granule environment for this proteolytic step. This conclusion is supported by the acute increase in active renin detected in the supernatants of co-transfected $GH_4C1$ cells treated for 20 min. with potassium chloride (FIG. 5), a de-polarizing agent which causes the release of secretory granules.[21]

Using a polyclonal antibody raised against a peptide derived from mouse PC5, we have studied the distribution of human PC5 in several human tissues (FIG. 6). To date, we have been unable to detect staining for PC5 in the human kidney, although our sections stain positively for renin. In the placental cotyledon, PC5 is located in the syncitiotrophoblast layer of the chorionic villi while anti-renin antibody stains primarily the chorionic mesoderm. In the adrenal gland, the antibodies against both renin and PC5 show a preferential staining of zona glomerulosa cells in the adrenal cortex (g) with very little staining of the capsule (c) and zona fasciculata (f). No staining was evident with omission of the first antibody (data not shown). Thus, our immunohistochemical studies would suggest that, of the three tissues studied, it is likely that prorenin and PC5 are only clearly co-localized in the zona glomerulosa of the human adrenal cortex.

DISCUSSION

In the present study, we describe the cloning and expression of the human prohormone convertase PC5 and its activity as a human PPE. Co-transfection assays in cultured cells demonstrates that hPC5 activates human prorenin with the expected site-specificity and that this cleavage most likely takes place in dense core secretory granules. In addition, immunohistochemistry of human tissues shows co-localization of hPC5 with renin in the zona glomerulosa of the adrenal cortex.

Several lines of evidence suggest that the human adrenal gland contains a physiologically important local RAS: First, RNA encoding angiotensinogen and renin have been detected in preparations from the human adrenal zona glomerulosa, fasciculata and medulla[24,25], confirming that both renin and its substrate are synthesized within the human adrenal gland. Second, ACE inhibition or blockade of angiotensin receptors inhibits aldosterone release from human adrenal tissue explants[26], suggesting that the local RAS plays an active role in the regulation of aldosterone secretion from the adrenal gland. Third, tissue explants of human adrenal cortex and aldosterone-secreting adenomas secrete small quantities of active renin[24,26,27], suggesting that the adrenal cortex expresses a PPE capable of activating human prorenin. Our current results suggest that PC5 could be the PPE responsible for activation of renin in the human adrenal cortex as both renin and hPC5 are immuno-detectable in the zona glomerulosa. Additional circumstantial evidence supports this conclusion: First, centrifugal fractionation of adrenal cortical cells reveals that renin is contained in the "granular" fraction, of intermediate density between vesicles and lysosomes.[28] As our current study suggests that PC5 only cleaves human prorenin in cells containing secretory granules, renin would be in the appropriate intracellular compartment to be activated by PC5 in the adrenal cortex. Second, rats transgenic for mouse Ren-2 renin [TGR(mRen-2)27] display fulminant hypertension[29] which correlates best with the expression of the mouse prorenin in the adrenal gland.[30–32] As previous studies have demonstrated that PC5 is capable of activating mouse Ren-2 prorenin, but not rat prorenin ([23]and data not shown) it is possible that the TGR(mRen-2)27 transgenic rat is a model for activation of a tissue RAS by the fortuitous juxtaposition of prorenin with an appropriate PPE in the adrenal cortex. These results also raise the possibility that the tissue-distribution of PPEs and their apparent selectivity in activating prorenin from different species could lead to differing functions of the tissue RAS between rodents and humans.

The principal source of circulating active renin in humans is the JG cells of the kidney. Although low levels of hPC5 RNA can be detected by Northern blot analysis in a sample of total kidney poly-A RNA (FIG. 3), we were unable to localize PC5 immunostaining in kidney sections (FIG. 6) raising the possibility that PC5 is expressed at low levels in diffuse cell types in the kidney. Thus, while these results do not formally rule out PC5 as a PPE in the kidney, our inability to detect it in JG cells makes it unlikely that it plays a major role in the production of renal renin. In contrast, relatively abundant amounts of PC5 mRNA and protein were detected in the placenta although evidence suggests that placental cells in culture[33] and in vivo[34] only secrete prorenin. However, immunostaining revealed that the cells producing PC5 and prorenin in the human placenta are distinct. It is also unlikely that PC5 would activate prorenin once the two proteins are secreted due to the apparent requirement of a granular environment for the cleavage of prorenin by hPC5 in transfected cells. Thus, in contrast to the case in the adrenal gland, it is unlikely that PC5 expressed in the human placenta would activate placental prorenin.

In the mouse, two forms of hPC5 have been predicted based on cloned cDNAs; the first would be analogous to the hPC5 cDNA described in this study and to that cloned from rat tissues[15,23] while the second, called PC6B, is extended at its 3'-end due to a differential RNA splicing event.[35] Although the hPC5 CDNA we have cloned is only roughly 3 Kb in length, the major RNA band seen in human tissues is of approximately 6.6 Kb. The identity of the longer band hybridizing to the hPC5 probe is currently unknown. It should be noted that neither of the CDNA clones isolated from a screening of 1.2 million phage from the adrenal library was extended at its 3'-end (FIG. 1), although the probes used in their isolation cover the region of homology with the mouse PC6B variant.[35] In mouse tissues, expression of the PC6B variant is restricted to few tissues[35] while the abundance of the 6.6 Kb detected with the hPC5 probe is directly proportional to the abundance of the 3.8 Kb band. Hybridization of RNA blots from rodent tissues using a PC5 probe also reveals RNA bands of 3.8, 6.5 and 7.5 Kb[15,35] and use of a PC5-specific probe reveals a band at 6.5 Kb. Thus, it is possible that additional PC5 RNA species exist in mammals that are extended at their 5'-ends. Alternatively, human tissues may be particularly enriched in a homologue to PC6B which was not picked up in our screenings. Recent data suggest that the alternate C-terminal tail present on PC6B may serve to retain the enzyme in the Golgi network, while the "short" form of mouse PC5 is targeted to dense core secretory granules (N. G. Seidah, unpublished). These data and the results of our co-transfection assays (FIG. 4) would suggest that the "short" form of hPC5 described here is the form which would be active in renin processing in secretory granules.

The PC5 enzymes isolated from humans and mice show a remarkably high degree of conservation at the nucleotide and protein sequence levels. This degree of similarity is higher than that seen for the other mammalian PC enzymes which seem to diverge in the C-terminal half of the enzyme.[36,37] This high degree of sequence conservation may reflect an essential function of PC5 (and the C-terminus of PC5) in mammals.

PC5 is Linked to Smooth Muscle Proliferation

To investigate which PC could be a potential target of smooth muscle cell proliferation, we tested if any of the PCs were affected in the process of restenosis, wherein such proliferation is observed. Changes in PC levels in the process of restenosis is a distinct possibility since in previous studies using animal models or cell lines, we have shown that PC levels can be regulated or even be induced. We thus obtained human restenosed coronary tissues from patients. These tissues were screened for each of the PC mRNAs using in vivo hybridization histochemistry in order to obtain information within an anatomical context. Coronaries with partial or total occlusions demonstrated dramatically increased PC5 MRNA levels within smooth muscle tissues, whereas coronary tissue without occlusions were PC5 negative. These results indicate that PC5 is either strongly up-regulated or induced in the human coronary arteries during the active process of stenosis (FIG. 7). To our knowledge this is the first indication that a specific PC is directly linked to smooth muscle proliferation.

These results suggested that if PC5 enzymatic activity could somehow be inhibited or the upregulation of PC5 MRNA could be prevented, this may attenuate or stop the process of restenosis. This could occur through the inhibition of the processing function of this enzyme on the numerous growth factors that are involved in the formation of the coronary lesion. If these growth factors are not processed they will remain biologically inactive. Our approach was to test the effectiveness of PC5 antisense inhibition on smooth muscle proliferation in vitro.

A specific antisense oligonucleotide (ODN) was shown to drastically inhibit smooth muscle proliferation using an in vitro model of rabbit smooth muscle in culture. Incubating rabbit smooth muscle cells with a PC5 antisense 17-mer oligonucleotide shown in Table 1 caused a dose-dependent inhibition smooth muscle proliferation with a maximal inhibitory effect of 81.6%+1.6% at 10 mM (mean of three experiments done in quadruplicates). This inhibitory effect is highly significant (P=0.0001) as compared to controls which included either a sense or a mismatched oligonucleotide used at the same concentration (see Table 1). In addition we found that the expression of PC5 is decreased in the affected cells (FIG. 8). When compared to other targets, such as c-myc, this approach was much more effective in inhibiting smooth muscle proliferation, as the best effects of antisense c-myc resulted in 71.7+3.5% (means of three experiment done in quadruplicate) inhibition (mean of three experiment done in quadruplicates). These results are indicative of an in vivo effect since silencing PC5 would impede muscle cell proliferation and restenosis.

Cholesterol Conjugation of Oligonucleotides

Phosphorothioate antisense ODNs were synthesized on a DNA/RNA synthesizer following standard procedure (Applied Biosystems). Conjugation of oligomers with cholesterol was achieved with 3'-cholesterol-VN CPG (Clontech), a virtual nucleotide (VN) glass reagent that introduces a cholesterol label to the 3' terminus of an oligonucleotide via solid-phase synthesis. When ODN synthesis. When ODN synthesis was completed, oligomers were removed from the column with 30% $NH_4OH$ (1 hour at room temperature), and then deprotected for 8 hours at 60° C. Oligos were purified and detritylated with oligonucleotide purification cartridges (Applied Biosystems), and then lyophilized with a centrifugal evaporator (Savant SpeedVac).

In Vivo Arterial ODN Transfection

New Zealand rabbits male or female (2 Kg) were intramuscularly sedated with xylazine (2 mg/Kg) and anesthetized with ketamine (100 mg/Kg) prior to surgical exposure of left carotid artery. Segments of 10 mm of carotids were transiently isolated by temporary ligatures and rinsed with 0.9% sodium chloride via a cannula until there was no more visible evidence of blood components. Carotid arteries were transfected with 80 μmol/L of antisense ODNs in a 1 cm portion either alone or conjugated to cholesterol for a period of 30 minutes. The volume infused was 100 μl, and no visible loss of volume was noted throughout the incubation period. Following transfection, the treated segments were rinsed with 0.9% sodium chloride (3×100 μl) and upon cannula removal, the arteriotomy site was repaired with microsutures, restoring normal blood flow and the neck wound closed. All experimental protocols in this project were approved by the Institutional Committee for Animal Protection of the Louis-Charles Simard Research Center.

Neointimal Hyperplasia Inhibition

A total of 36 New Zealand white rabbit carotid arteries were injured with a 2.5 mm balloon catheter serially inflated for 1 minute to 4, 6, 8 and 10 atm with gentle traction, allowing 45 seconds between inflations. Two weeks later, a second injury was imposed at the same arterial site which was then transfected in a 1 cm portion with 80 μmol/L (100 μl of volume injected) of therapeutic molecules or with 100 μL of NaCl 0.9% as control. Intimal/medial areas were evaluated by computer analysis on histological sections derived from transfected arteries two weeks following the second injury and transfection procedure.

The addition of a PC5 antisense 17-mer ODN shown in Table 1 at the time of a second carotid injury with a balloon catheter decreased carotid stenosis, measured as area ratio intima/media, by 40% (Area ratio intima/media sense ODN minus area ratio antisense ODN divided by area ratio sense ODN; see FIG. 9). This inhibitory effect is highly significant (P 0.0118 and P=0.0078) as compared to the sense and random controls, respectively. These results are the basis of a method of preventing stenosis comprising administering an effective stenosis inhibitory dose of a PC5 antisense to a subject in need for such a treatment. Other antisense oligonucleotides may be added to optimize this method of preventing restenosis, such as those silencing the expression of other convertases, namely PC2, which are also observed in atherectomy specimens (see FIG. 10).

The development of drugs based on the inhibition or the inactivation of the convertases is of great interest because the drugs can easily be delivered directly at the affected site during the intervention by the cardiologist.

In addition we claim that this therapeutic approach, based on the inhibition of cell growth by antisense against one of the convertases will be applicable to all proliferative diseases involving maturation of a given proteic precursor into an active protein:

TABLE 1

The sequences of the oligonucleotides used are:

| | | |
|---|---|---|
| Antisense | GCAACTTGCCAGAGCAT | SEQ ID NO: 3 |
| Sense | ATGCTCTGGCAAGTTGC | SEQ ID NO. 4 |
| Random | AATCCGTGAGACCAGTC | SEQ ID NO. 5. |

PC5 is Involved in the Cleavage of HIV gp160 into gp120 and gp41

As mentioned above, PC5, PC7 and furin are known to be present in $CD4^+$ T lymphocytes. All three enzymes cleave HIV gp160 to gp120 and gp41 as well as a synthetic peptide covering the junction wherein cleavage occurs in gp160. Since the 17-mer antisense ODN defined in Seq ID. No. 3 successfully silenced the expression of PC5 and prevented restenosis, the same oligonucleotide as well as any other oligonucleotide or construct having an equivalent silencing function will find use in inhibiting the action of PC5 on HIV gp160 in $CD4^+$ T lymphocytes. To optimize the inhibition of conversion of gp160 into its fusiogenic form, a cocktail comprising antisense molecules to PC5, PC7 and furin is contemplated as part of the present invention. Appropriate vehicles such as liposomes may be used to deliver these antisense molecules to the target tissues.

This invention has been described hereinbelow. It may be apparent to the skilled reader that modifications can be made thereto without departing from the above teachings. These modifications are considered as part of the scope of the present invention, as defined in the appended claims.

REFERENCES

1. Frohlich E D, Iwata T, Sasaki 0. Clinical and physiologic significance of local tissue renin-angiotensin systems. *Am J Med*. 1990;87 (suppl 6B):6B-19S-6B-23S
2. Johnston C I, Burrell L M, Perich R, Jandeleit K, Jackson B. The tissue renin-angiotensin system and its functional role. *Clin Exper Pharmacol Physiol*. 1992;19:1–5
3. Gardner D G, Gertz B J, Deschepper C F, Kim D Y. Gene for the rat atrial natriuretic peptide is regulated by glucocorticoids in vitro. *J Clin Invest*. 1988;82:1275–1281
4. Lee M A, Bohm M, Paul M, Ganten D. Tissue renin-angiotensin systems. Their role in cardiovascular disease. *Circulation*. 1993;87:IV7–I13
5. Do Y S, Shinagawa T, Tam H, Inagami T, Hsueh W A. Characterization of pure human renal renin. *J Biol Chem*. 1987;262:1037–1043
6. Taugner R, Kim S J, Murakami K, Waldherr R. The fate of prorenin during granulopoiesis in epithelioid cells. Immunocytochemical experiments with antisera against renin and different portions of the renin prosegment. *Histochemistry*. 1987;86:249–253
7. Taugner R, Hackenthal E. On the character of the secretory granules in juxtaglomerular epithelioid cells. *Int Rev Cytol*. 1988;110:93–131
8. Saint-Andre J P, Rohmer V, Pinet F, Rousselet M C, Bigorgne J C, Corvol P. Renin and cathepsin B in human pituitary lactotroph cells. An ultrastructural study. *Histochemistry*. 1989;91:291–297
9. Wang P H, Do Y S, Macaulay L, Shinagawa T, Anderson P W, Baxter J D, Hsueh W A. Identification of renal cathepsin B as a human prorenin-processing enzyme. *J Biol Chem*. 1991;266:12633–12638
10. Benjannet S, Reudelhuber T, Mercure C, Rondeau N, Chretien M, Seidah N G. Proprotein conversion is determined by a multiplicity of factors including convertase processing, substrate specificity, and intracellular environment. Cell type-specific processing of human prorenin by the convertase PC1. *J Biol Chem*. 1992;267:11417–11423
11. Konoshita T, Gasc J M, Villard E, Takeda R, Seidah N G, Corvol P, Pinet F. Expression of PC2 and PC1/PC3 in human pheochromocytomas. *Mol Cell Endocrinol*. 1994;99:307–314
12. Reudelhuber T L, Ramla D, Chiu L, Mercure C, Seidah N G. Proteolytic processing of human prorenin in renal and non-renal tissues. *Kidney Int*. 1994;46:1522–1524
13. Sigmund C D, Okuyama K, Ingelfinger J, Jones C A, Mullins J J, Kane C, Kim U, Wu C Z, Kenny L, Rustum Y, Dzau V J, Gross K W. Isolation and characterization of renin-expressing cell lines from transgenic mice containing a renin-promoter viral oncogene fusion construct. *J Biol Chem*. 1990;265:19916–19922
14. Sambrook J, Fritsch E F, Maniatis T. *Molecular cloning: A laboratory manual*. Cold Spring Harbor, N.Y.: Cold Spring Harbor Laboratory Press, 1989;
15. Lusson J, Vieau D, Hamelin J, Day R, Chretien M, Seidah N G. cDNA structure of the mouse and rat subtilisin/kexin-like PC5: a candidate proprotein convertase expressed in endocrine and nonendocrine cells. *Proc Natl Acad Sci USA*. 1993;90:6691–6695
16. *Current Protocols in Molecular Biology*. New York: John Wiley and Sons, Inc. 1996;
17. Day R, Schafer M K, Watson S J, Chretien M, Seidah N G. Distribution and regulation of the prohormone convertases PC1 and PC2 in the rat pituitary. *Molec Endocrinol*. 1992;6:485–497
18. Horton R M, Hunt H D, Ho S N, Pullen J K, Pease L R. Engineering hybrid genes without the use of restriction enzymes: gene splicing by overlap extension. *Gene*. 1989;77:61–68
19. Chu W N, Baxter J D, Reudelhuber T L. A targeting sequence for dense core secretory granules resides in the protein moiety of human prorenin. *Molec Endocrinol*. 1990;4:1905–1913
20. Chu W N, Mercure C, Baxter J D, Reudelhuber T L. Molecular determinants of human prorenin processing. *Hypertension*. 1992;20:782–787
21. Scammell J G, Burrage T G, Dannies P S. Hormonal induction of secretory granules in a pituitary tumor cell line. *Endocrinology*. 1986;119:1543–1548
22. Ghitescu L, Bendayan M. Immunolabeling efficiency of protein A-gold complexes. *J Histochem Cytochem*. 1990;38:1523–1530
23. Nakagawa T, Hosaka M, Torii S, Watanabe T, Murakami K, Nakayama K. Identification and functional expression of a new member of the mammalian Kex2-like processing endoprotease family: Its striking structural similarity to PACE-4. *J Biochem*. 1993;113:132–135
24. Racz K, Pinet F, Gasc J M, Guyene T T, Corvol P. Coexpression of renin, angiotensinogen, and their messenger ribonucleic acids in adrenal tissues. *J Clin Endocrinol Metab*. 1992;75:730–737
25. Paul M, Wagner J, Dzau V J. Gene expression of the renin-angiotensin system in human tissues. Quantitative analysis by the polymerase chain reaction. *J Clin Invest*. 1993;91:2058–2064
26. Fallo F, Pistorello M, Pedini F, D'Agostino D, Mantero F, Boscaro M. in vitro evidence for local generation of renin and angiotensin II/III immunoreactivity by the human adrenal gland. *Acta Endocrinologica.* 1991;125:319–330
27. Sarzani R, Fallo F, Dessi-Fulgheri P, Pistorello M, Lanari A, Paci VM, Mantero F, Rappelli A. Local renin-angiotensin system in human adrenals and aldosteronomas. *Hypertension.* 1992;19:702–707
28. Mizuno K, Hoffman L H, McKenzie J C, Inagami T. Presence of renin secretory granules in rat adrenal gland and stimulation of renin secretion by angiotensin II but not by adrenocorticotropin. *J Clin Invest.* 1988;82:1007–1016
29. Mullins J J, Peters J, Ganten D. Fulminant hypertension in transgenic rats harbouring the mouse Ren-2 gene. *Nature.* 1990;344:541–544
30. Yamaguchi T, Tokita Y, Franco-Saenz R, Mulrow P J, Peters J, Ganten D. Zonal distribution and regulation of adrenal renin in a transgenic model of hypertension in the rat. *Endocrinology.* 1992;131:1955–1962
31. Rocco S, Rebuffat P, Cimolato M, Opocher G, Peters J, Mazzocchi G, Ganten D, Mantero F, Nussdorfer G G. Zona glomerulosa of the adrenal gland in a transgenic strain of rat: a morphologic and functional study. *Cell & Tiss Res.* 1994;278:21–28
32. Tokita Y, Franco-Saenz R, Mulrow P J, Ganten D. Effects of nephrectomy and adrenalectomy on the renin-angiotensin system of transgenic rats TGR(mRen2)27. *Endocrinology.* 1994;134:253–257
33. Duncan K G, Haidar M A, Baxter J D, Reudelhuber T L. Regulation of human renin expression in chorion cell primary cultures. *Proc Natl Acad Sci USA.* 1990;87:7588–7592
34. Lenz T, James G D, Laragh J H, Sealey J E. Prorenin secretion from human placenta perfused in vitro. *Am J Physiol.* 1991;260:E876-E882
35. Nakagawa T, Murakami K, Nakayama K. Identification of an isoform with an extremely large Cys-rich region of PC6, a Kex2-like processing endoprotease. *FEBS Lett.* 1993;327:165–171
36. Seidah N G, Hamelin J, Gaspar A M, Day R, Chretien M. The cDNA sequence of the human pro-hormone and pro-protein convertase PC1. *DNA & Cell Biology.* 1992;11:283–289
37. Seidah N G, Day R, Marcinkiewicz M, Chretien M. Mammalian paired basic amino acid convertases of pro-hormones and proproteins. *Ann NY Acad Sci.* 1993;680:135–146
38. Miranda L, Wolf J, Pichuantes S, Duke R, Franzusoff A. Isolation of the human PC6 gene encoding the putative host proteas for HIV-1 gp160 processing in CD4[+] T lymphocytes. *Proc. Natl. Acad. Sci. USA* 1996;93:7695–7700.

The embodiments of the invention in which an exclusive property or privilege is claimed are defined as follows:

1. A method for reducing restenosis occurring at an injured vascular site comprising administering at said site an effective amount of an antisense nucleic acid having a nucleotide sequence as set forth in SEQ ID NO: 3 to suppress expression of pro-protein converting enzyme 5 (PC5) gene or to inhibit PC5 activity.

2. A composition for reducing restenosis at an injured vascular site comprising an effective amount of an antisense nucleic acid having a nucleotide sequence as set forth in SEQ ID NO: 3 to suppress expression of pro-protein converting enzyme 5 (PC5) gene or to inhibit PC5 activity at said site and a suitable pharmaceutical carrier.

3. The method of claim 1 wherein said antisense nucleic acid is administered to said injured vascular site by means of a cannula.

* * * * *

UNITED STATES PATENT AND TRADEMARK OFFICE
CERTIFICATE OF CORRECTION

PATENT NO. : 6,380,171 B1
DATED : April 30, 2002
INVENTOR(S) : Robert Day et al.

It is certified that error appears in the above-identified patent and that said Letters Patent is hereby corrected as shown below:

Title page,
Item [57], ABSTRACT,
Line 2, "CDNA" should read -- cDNA --.

Column 2,
Line 41, "theses" should read -- these --.

Column 3,
Line 28, "CDNA" should read -- cDNA --.
Line 45, delete "is".
Line 54, "proren+pUC" should read -- proren + pUC --.
Line 61, "$CH_4C_1$" should read -- $CH_4Cl$ --.

Column 4,
Line 14, "MRNA" should read -- mRNA --.
Lines 58 and 66, "CDNA" should read -- cDNA --.
Line 60, "$PCS.^{15}$" should read -- $PC5.^{15}$ --.
Line 61, "$^{32}pdCTP$" should read -- $^{32}PdCTP$ --.
Line 67, "PCS" should read -- PC5 --.

Column 5,
Lines 3, 34 and 45, "CDNA" should read -- cDNA --.
Line 29, "MRNA" should read -- mRNA --.

Column 6,
Lines 44 and 50, "CDNA" should read -- cDNA --.

Column 8,
Lines 53 and 57, "CDNA" should read -- cDNA --.

Column 9,
Lines 34 and 43, "MRNA" should read -- mRNA --.

Column 10,
Lines 11 and 12, delete first sentence: "When ODN synthesis".
Line 55, "PO.0118" should read -- P=0.0118 --.

UNITED STATES PATENT AND TRADEMARK OFFICE
CERTIFICATE OF CORRECTION

PATENT NO. : 6,380,171 B1
DATED : April 30, 2002
INVENTOR(S) : Robert Day et al.

It is certified that error appears in the above-identified patent and that said Letters Patent is hereby corrected as shown below:

<u>Column 37,</u>
Line 14, "of pro-protein" should read -- of human pro-protein --.
Line 15, "inhibit PC5" should read -- inhibit human PC5 --.

<u>Column 38,</u>
Line 9, "of pro-protein" should read -- of human pro-protein --.
Line 10, "inhibit PC5" should read -- inhibit human PC5 --.

Signed and Sealed this

Third Day of December, 2002

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 2819
<212> TYPE: DNA
<213> ORGANISM: Homo sapiens
<220> FEATURE:
<221> NAME/KEY: CDS
<222> LOCATION: (1)..(2745)

<400> SEQUENCE: 1

```
atg gac tgg gac tgg ggg aac cgc tgc agc cgc ccg gga cgg cgg gat      48
Met Asp Trp Asp Trp Gly Asn Arg Cys Ser Arg Pro Gly Arg Arg Asp
 1               5                  10                  15 ctg ctg tgc gtg ctg gcg ctg ctc ggg ggc tgc ctg ctc ccc gtg tgt      96
Leu Leu Cys Val Leu Ala Leu Leu Gly Gly Cys Leu Leu Pro Val Cys
                20                  25                  30 cgg acg cgc gtc tac acc aac cac tgg gca gtc aaa atc gcc ggg ggc     144
Arg Thr Arg Val Tyr Thr Asn His Trp Ala Val Lys Ile Ala Gly Gly
            35                  40                  45 ttc ccg gag gcc aac cgt atc gcc agc aag tac gga ttc atc aac ata     192
Phe Pro Glu Ala Asn Arg Ile Ala Ser Lys Tyr Gly Phe Ile Asn Ile
        50                  55                  60 gga cag ata ggg gcc ctg aag gac tac tac cac ttc tac cat agc agg     240
Gly Gln Ile Gly Ala Leu Lys Asp Tyr Tyr His Phe Tyr His Ser Arg
 65                  70                  75                  80 acg att aaa agg tca gtt atc tcg agc aga ggg acc cac agt ttc att     288
Thr Ile Lys Arg Ser Val Ile Ser Ser Arg Gly Thr His Ser Phe Ile
                 85                  90                  95 tca atg gaa cca aag gtg gaa tgg atc caa cag caa gtg gta aaa aag     336
Ser Met Glu Pro Lys Val Glu Trp Ile Gln Gln Gln Val Val Lys Lys
                100                 105                 110 cgg aca aag agg gat tat gac ttc agt cgt gcc cag tct acc tat ttc     384
Arg Thr Lys Arg Asp Tyr Asp Phe Ser Arg Ala Gln Ser Thr Tyr Phe
```

```
                115                 120                 125
aat gat ccc aag tgg ccc agc atg tgg tat atg cac tgc agt gac aat     432
Asn Asp Pro Lys Trp Pro Ser Met Trp Tyr Met His Cys Ser Asp Asn
        130                 135                 140 aca cat ccc tgc cag tct gac atg aat atc gaa gga gcc tgg aag aga     480
Thr His Pro Cys Gln Ser Asp Met Asn Ile Glu Gly Ala Trp Lys Arg
145                 150                 155                 160 ggc tac acg gga aag aac att gtg gtc act atc ctg gat gac gga att     528
Gly Tyr Thr Gly Lys Asn Ile Val Val Thr Ile Leu Asp Asp Gly Ile
                165                 170                 175 gag aga acc cat cca gat ctg atg caa aac tac gat gct ctg gca agt     576
Glu Arg Thr His Pro Asp Leu Met Gln Asn Tyr Asp Ala Leu Ala Ser
        180                 185                 190 tgc gac gtg aat ggg aat gac ttg gac cca atg cct cgt tat gat gca     624
Cys Asp Val Asn Gly Asn Asp Leu Asp Pro Met Pro Arg Tyr Asp Ala
                195                 200                 205 agc aac gag aac aag cat ggg act cgc tgt gct gga gaa gtg gca gcc     672
Ser Asn Glu Asn Lys His Gly Thr Arg Cys Ala Gly Glu Val Ala Ala
        210                 215                 220 gct gca aac aat tcg cac tgc aca gtc gga att gct ttc aac gcc aag     720
Ala Ala Asn Asn Ser His Cys Thr Val Gly Ile Ala Phe Asn Ala Lys
225                 230                 235                 240 atc gga gga gtg cga atg ctg gac gga gat gtc acg gac atg gtt gaa     768
Ile Gly Gly Val Arg Met Leu Asp Gly Asp Val Thr Asp Met Val Glu
                245                 250                 255 gca aaa tca gtt agc ttc aac ccc cag cac gtg cac att tac agc gcc     816
Ala Lys Ser Val Ser Phe Asn Pro Gln His Val His Ile Tyr Ser Ala
        260                 265                 270 agc tgg ggc ccg gat gat gat ggc aag act gtg gac gga cca gcc ccc     864
Ser Trp Gly Pro Asp Asp Asp Gly Lys Thr Val Asp Gly Pro Ala Pro
        275                 280                 285 ctc acc cgg caa gcc ttt gaa aac ggc gtt aga atg ggg cgg aga ggc     912
Leu Thr Arg Gln Ala Phe Glu Asn Gly Val Arg Met Gly Arg Arg Gly
        290                 295                 300 ctc ggc tct gtg ttt gtt tgg gca tct gga aat ggt gga agg agc aaa     960
Leu Gly Ser Val Phe Val Trp Ala Ser Gly Asn Gly Gly Arg Ser Lys
305                 310                 315                 320 gac cac tgc tcc tgt gat ggc tac acc aac agc atc tac acc atc tcc    1008
Asp His Cys Ser Cys Asp Gly Tyr Thr Asn Ser Ile Tyr Thr Ile Ser
                325                 330                 335 atc agc agc act gca gaa agc gga aag aaa cct tgg tac ctg gaa gag    1056
Ile Ser Ser Thr Ala Glu Ser Gly Lys Lys Pro Trp Tyr Leu Glu Glu
        340                 345                 350 tgt tca tcc acg ctg gcc aca acc tac agc agc ggg gag tcc tac gat    1104
Cys Ser Ser Thr Leu Ala Thr Thr Tyr Ser Ser Gly Glu Ser Tyr Asp
        355                 360                 365 aag aaa atc atc act aca gat ctg agg cag cgt tgc acg gac aac cac    1152
Lys Lys Ile Ile Thr Thr Asp Leu Arg Gln Arg Cys Thr Asp Asn His
        370                 375                 380 act ggg acg tca gcc tca gcc ccc atg gct gca ggc atc att gcg ctg    1200
Thr Gly Thr Ser Ala Ser Ala Pro Met Ala Ala Gly Ile Ile Ala Leu
385                 390                 395                 400 gcc ctg gaa gcc aat ccg ttt ctg acc tgg aga gac gta cag cat gtt    1248
Ala Leu Glu Ala Asn Pro Phe Leu Thr Trp Arg Asp Val Gln His Val
                405                 410                 415 att gtc agg act tcc cgt gcg gga cat ttg aac gct aat gac tgg aaa    1296
Ile Val Arg Thr Ser Arg Ala Gly His Leu Asn Ala Asn Asp Trp Lys
                420                 425                 430 acc aat gct gct ggt ttt aag gtg agc cat ctt tat gga ttt gga ctg    1344
```

```
                                                        -continued

Thr Asn Ala Ala Gly Phe Lys Val Ser His Leu Tyr Gly Phe Gly Leu
        435                 440                 445 atg gac gca gaa gcc atg gtg atg gag gca gag aag tgg acc acc gtt         1392
Met Asp Ala Glu Ala Met Val Met Glu Ala Glu Lys Trp Thr Thr Val
450                 455                 460 ccc cgg cag cac gtg tgt gtg gag agc aca gac cga caa atc aag aca         1440
Pro Arg Gln His Val Cys Val Glu Ser Thr Asp Arg Gln Ile Lys Thr
465                 470                 475                 480 atc cgc cct aac agt gca gtg cgc tcc atc tac aaa gct tca ggc tgc         1488
Ile Arg Pro Asn Ser Ala Val Arg Ser Ile Tyr Lys Ala Ser Gly Cys
            485                 490                 495 tcg gat aac ccc aac cgc cat gtc aac tac ctg gag cac gtc gtt gtg         1536
Ser Asp Asn Pro Asn Arg His Val Asn Tyr Leu Glu His Val Val Val
            500                 505                 510 cgc atc acc atc acc cac ccc agg aga gga gac ctg gcc atc tac ctg         1584
Arg Ile Thr Ile Thr His Pro Arg Arg Gly Asp Leu Ala Ile Tyr Leu
        515                 520                 525 acc tcg ccc tct gga act agg tct cag ctt ttg gcc aac agg cta ttt         1632
Thr Ser Pro Ser Gly Thr Arg Ser Gln Leu Leu Ala Asn Arg Leu Phe
530                 535                 540 gat cac tcc atg gaa gga ttc aaa aac tgg gag ttc atg acc att cat         1680
Asp His Ser Met Glu Gly Phe Lys Asn Trp Glu Phe Met Thr Ile His
545                 550                 555                 560 tgc tgg gga gaa aga gct gct ggt gac tgg gtc ctt gaa gtt tat gat         1728
Cys Trp Gly Glu Arg Ala Ala Gly Asp Trp Val Leu Glu Val Tyr Asp
            565                 570                 575 act ccc tct cag cta agg aac ttt aag act cca ggt aaa ttg aaa gaa         1776
Thr Pro Ser Gln Leu Arg Asn Phe Lys Thr Pro Gly Lys Leu Lys Glu
            580                 585                 590 tgg tct ttg gtc ctc tac ggc acc tcc gtg cag cca tat tca cca acc         1824
Trp Ser Leu Val Leu Tyr Gly Thr Ser Val Gln Pro Tyr Ser Pro Thr
        595                 600                 605 aat gaa ttt ccg aaa gtg gaa cgg ttc cgc tat agc cga gtt gaa gac         1872
Asn Glu Phe Pro Lys Val Glu Arg Phe Arg Tyr Ser Arg Val Glu Asp
610                 615                 620 ccc aca gac gac tat ggc aca gag gat tat gca ggt ccc tgc gac cct         1920
Pro Thr Asp Asp Tyr Gly Thr Glu Asp Tyr Ala Gly Pro Cys Asp Pro
625                 630                 635                 640 gag tgc agt gag gtt ggc tgt gac ggg cca gga cca gac cac tgc aat         1968
Glu Cys Ser Glu Val Gly Cys Asp Gly Pro Gly Pro Asp His Cys Asn
            645                 650                 655 gac tgt ttg cac tac tac tac aag ctg aaa aac aat acc agg atc tgt         2016
Asp Cys Leu His Tyr Tyr Tyr Lys Leu Lys Asn Asn Thr Arg Ile Cys
            660                 665                 670 gtc tcc agc tgc ccc cct ggc cac tac cac gcc gac aag aag cgc tgc         2064
Val Ser Ser Cys Pro Pro Gly His Tyr His Ala Asp Lys Lys Arg Cys
        675                 680                 685 agg aag tgt gcc ccc aac tgt gag tcc tgc ttt ggg agc cat ggt gac         2112
Arg Lys Cys Ala Pro Asn Cys Glu Ser Cys Phe Gly Ser His Gly Asp
690                 695                 700 caa tgc atg tcc tgc aaa tat gga tac ttt ctg aat gaa gaa acc aac         2160
Gln Cys Met Ser Cys Lys Tyr Gly Tyr Phe Leu Asn Glu Glu Thr Asn
705                 710                 715                 720 agc tgt gtt act cac tgc cct gat ggg tca tat cag gat acc aag aaa         2208
Ser Cys Val Thr His Cys Pro Asp Gly Ser Tyr Gln Asp Thr Lys Lys
            725                 730                 735 aat ctt tgc cgg aaa tgc agt gaa aac tgc aag aca tgt act gaa ttc         2256
Asn Leu Cys Arg Lys Cys Ser Glu Asn Cys Lys Thr Cys Thr Glu Phe
            740                 745                 750
```

-continued

```
cat aac tgt aca gaa tgt agg gat ggg tta agc ctg cag gga tcc cgg    2304
His Asn Cys Thr Glu Cys Arg Asp Gly Leu Ser Leu Gln Gly Ser Arg
        755                 760                 765 tgc tct gtc tcc tgt gaa gat gga cgg tat ttc aac ggc cag gac tgc    2352
Cys Ser Val Ser Cys Glu Asp Gly Arg Tyr Phe Asn Gly Gln Asp Cys
770                 775                 780 cag ccc tgc cac cgc ttc tgc gcc act tgt gct ggg gca gga gct gat    2400
Gln Pro Cys His Arg Phe Cys Ala Thr Cys Ala Gly Ala Gly Ala Asp
785                 790                 795                 800 ggg tgc att aac tgc aca gag ggc tac ttc atg gag gat ggg aga tgc    2448
Gly Cys Ile Asn Cys Thr Glu Gly Tyr Phe Met Glu Asp Gly Arg Cys
            805                 810                 815 gtg cag agc tgt agt atc agc tat tac ttt gac cac tct tca gag aat    2496
Val Gln Ser Cys Ser Ile Ser Tyr Tyr Phe Asp His Ser Ser Glu Asn
        820                 825                 830 gga tac aaa tcc tgc aaa aaa tgt gat atc agt tgt ttg acg tgc aat    2544
Gly Tyr Lys Ser Cys Lys Lys Cys Asp Ile Ser Cys Leu Thr Cys Asn
    835                 840                 845 ggc cca gga ttc aag aac tgt aca agc tgc cct agt ggg tat ctc tta    2592
Gly Pro Gly Phe Lys Asn Cys Thr Ser Cys Pro Ser Gly Tyr Leu Leu
850                 855                 860 gac tta gga atg tgt caa atg gga gcc att tgc aag gat gca acg gaa    2640
Asp Leu Gly Met Cys Gln Met Gly Ala Ile Cys Lys Asp Ala Thr Glu
865                 870                 875                 880 gag tcc tgg gcg gaa gga ggc ttc tgt atg ctt gtg aaa aag aac aat    2688
Glu Ser Trp Ala Glu Gly Gly Phe Cys Met Leu Val Lys Lys Asn Asn
            885                 890                 895 ctg tgc caa cgg aag gtt ctt caa caa ctt tgc tgc aaa aca tgt aca    2736
Leu Cys Gln Arg Lys Val Leu Gln Gln Leu Cys Cys Lys Thr Cys Thr
        900                 905                 910 ttt caa ggc tgagcagcca tcttagattt ctttgttcct gtagacttat            2785
Phe Gln Gly
        915 agattattcc atattattaa aagaaaaaa aaaa                               2819

<210> SEQ ID NO 2
<211> LENGTH: 915
<212> TYPE: PRT
<213> ORGANISM: Homo sapiens

<400> SEQUENCE: 2

Met Asp Trp Asp Trp Gly Asn Arg Cys Ser Arg Pro Gly Arg Arg Asp
1               5                   10                  15

Leu Leu Cys Val Leu Ala Leu Leu Gly Gly Cys Leu Leu Pro Val Cys
                20                  25                  30

Arg Thr Arg Val Tyr Thr Asn His Trp Ala Val Lys Ile Ala Gly Gly
            35                  40                  45

Phe Pro Glu Ala Asn Arg Ile Ala Ser Lys Tyr Gly Phe Ile Asn Ile
        50                  55                  60

Gly Gln Ile Gly Ala Leu Lys Asp Tyr His Phe Tyr His Ser Arg
65                  70                  75                  80

Thr Ile Lys Arg Ser Val Ile Ser Ser Arg Gly Thr His Ser Phe Ile
                85                  90                  95

Ser Met Glu Pro Lys Val Glu Trp Ile Gln Gln Val Val Lys Lys
                100                 105                 110

Arg Thr Lys Arg Asp Tyr Asp Phe Ser Arg Ala Gln Ser Thr Tyr Phe
            115                 120                 125

Asn Asp Pro Lys Trp Pro Ser Met Trp Tyr Met His Cys Ser Asp Asn
```

-continued

```
            130                 135                 140
Thr His Pro Cys Gln Ser Asp Met Asn Ile Glu Gly Ala Trp Lys Arg
145                 150                 155                 160

Gly Tyr Thr Gly Lys Asn Ile Val Val Thr Ile Leu Asp Asp Gly Ile
                165                 170                 175

Glu Arg Thr His Pro Asp Leu Met Gln Asn Tyr Asp Ala Leu Ala Ser
                180                 185                 190

Cys Asp Val Asn Gly Asn Asp Leu Asp Pro Met Pro Arg Tyr Asp Ala
            195                 200                 205

Ser Asn Glu Asn Lys His Gly Thr Arg Cys Ala Gly Glu Val Ala Ala
            210                 215                 220

Ala Ala Asn Asn Ser His Cys Thr Val Gly Ile Ala Phe Asn Ala Lys
225                 230                 235                 240

Ile Gly Gly Val Arg Met Leu Asp Gly Asp Val Thr Asp Met Val Glu
                245                 250                 255

Ala Lys Ser Val Ser Phe Asn Pro Gln His Val His Ile Tyr Ser Ala
                260                 265                 270

Ser Trp Gly Pro Asp Asp Asp Gly Lys Thr Val Asp Gly Pro Ala Pro
            275                 280                 285

Leu Thr Arg Gln Ala Phe Glu Asn Gly Val Arg Met Gly Arg Arg Gly
290                 295                 300

Leu Gly Ser Val Phe Val Trp Ala Ser Gly Asn Gly Gly Arg Ser Lys
305                 310                 315                 320

Asp His Cys Ser Cys Asp Gly Tyr Thr Asn Ser Ile Tyr Thr Ile Ser
                325                 330                 335

Ile Ser Ser Thr Ala Glu Ser Gly Lys Lys Pro Trp Tyr Leu Glu Glu
                340                 345                 350

Cys Ser Ser Thr Leu Ala Thr Thr Tyr Ser Ser Gly Glu Ser Tyr Asp
            355                 360                 365

Lys Lys Ile Ile Thr Thr Asp Leu Arg Gln Arg Cys Thr Asp Asn His
            370                 375                 380

Thr Gly Thr Ser Ala Ser Ala Pro Met Ala Ala Gly Ile Ile Ala Leu
385                 390                 395                 400

Ala Leu Glu Ala Asn Pro Phe Leu Thr Trp Arg Asp Val Gln His Val
                405                 410                 415

Ile Val Arg Thr Ser Arg Ala Gly His Leu Asn Ala Asn Asp Trp Lys
                420                 425                 430

Thr Asn Ala Ala Gly Phe Lys Val Ser His Leu Tyr Gly Phe Gly Leu
            435                 440                 445

Met Asp Ala Glu Ala Met Val Met Glu Ala Glu Lys Trp Thr Thr Val
            450                 455                 460

Pro Arg Gln His Val Cys Val Glu Ser Thr Asp Arg Gln Ile Lys Thr
465                 470                 475                 480

Ile Arg Pro Asn Ser Ala Val Arg Ser Ile Tyr Lys Ala Ser Gly Cys
                485                 490                 495

Ser Asp Asn Pro Asn Arg His Val Asn Tyr Leu Glu His Val Val Val
            500                 505                 510

Arg Ile Thr Ile Thr His Pro Arg Arg Gly Asp Leu Ala Ile Tyr Leu
            515                 520                 525

Thr Ser Pro Ser Gly Thr Arg Ser Gln Leu Leu Ala Asn Arg Leu Phe
            530                 535                 540

Asp His Ser Met Glu Gly Phe Lys Asn Trp Glu Phe Met Thr Ile His
545                 550                 555                 560
```

-continued

```
Cys Trp Gly Glu Arg Ala Ala Gly Asp Trp Val Leu Glu Val Tyr Asp
                565                 570                 575
Thr Pro Ser Gln Leu Arg Asn Phe Lys Thr Pro Gly Lys Leu Lys Glu
            580                 585                 590
Trp Ser Leu Val Leu Tyr Gly Thr Ser Val Gln Pro Tyr Ser Pro Thr
        595                 600                 605
Asn Glu Phe Pro Lys Val Glu Arg Phe Arg Tyr Ser Arg Val Glu Asp
    610                 615                 620
Pro Thr Asp Asp Tyr Gly Thr Glu Asp Tyr Ala Gly Pro Cys Asp Pro
625                 630                 635                 640
Glu Cys Ser Glu Val Gly Cys Asp Gly Pro Gly Pro Asp His Cys Asn
                645                 650                 655
Asp Cys Leu His Tyr Tyr Tyr Lys Leu Lys Asn Asn Thr Arg Ile Cys
            660                 665                 670
Val Ser Ser Cys Pro Pro Gly His Tyr His Ala Asp Lys Lys Arg Cys
        675                 680                 685
Arg Lys Cys Ala Pro Asn Cys Glu Ser Cys Phe Gly Ser His Gly Asp
    690                 695                 700
Gln Cys Met Ser Cys Lys Tyr Gly Tyr Phe Leu Asn Glu Glu Thr Asn
705                 710                 715                 720
Ser Cys Val Thr His Cys Pro Asp Gly Ser Tyr Gln Asp Thr Lys Lys
                725                 730                 735
Asn Leu Cys Arg Lys Cys Ser Glu Asn Cys Lys Thr Cys Thr Glu Phe
            740                 745                 750
His Asn Cys Thr Glu Cys Arg Asp Gly Leu Ser Leu Gln Gly Ser Arg
        755                 760                 765
Cys Ser Val Ser Cys Glu Asp Gly Arg Tyr Phe Asn Gly Gln Asp Cys
    770                 775                 780
Gln Pro Cys His Arg Phe Cys Ala Thr Cys Ala Gly Ala Gly Ala Asp
785                 790                 795                 800
Gly Cys Ile Asn Cys Thr Glu Gly Tyr Phe Met Glu Asp Gly Arg Cys
                805                 810                 815
Val Gln Ser Cys Ser Ile Ser Tyr Tyr Phe Asp His Ser Ser Glu Asn
            820                 825                 830
Gly Tyr Lys Ser Cys Lys Lys Cys Asp Ile Ser Cys Leu Thr Cys Asn
        835                 840                 845
Gly Pro Gly Phe Lys Asn Cys Thr Ser Cys Pro Ser Gly Tyr Leu Leu
    850                 855                 860
Asp Leu Gly Met Cys Gln Met Gly Ala Ile Cys Lys Asp Ala Thr Glu
865                 870                 875                 880
Glu Ser Trp Ala Glu Gly Gly Phe Cys Met Leu Val Lys Lys Asn Asn
                885                 890                 895
Leu Cys Gln Arg Lys Val Leu Gln Leu Cys Cys Lys Thr Cys Thr
            900                 905                 910
Phe Gln Gly
        915
```

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:synthetic

<400> SEQUENCE: 3

-continued

```
gcaacttgcc agagcat                                                    17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:synthetic

<400> SEQUENCE: 4
atgctctggc aagttgc                                                    17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:synthetic

<400> SEQUENCE: 5
aatccgtgag accagtc                                                    17

<210> SEQ ID NO 6
<211> LENGTH: 2766
<212> TYPE: DNA
<213> ORGANISM: Homo sapiens
<220> FEATURE:
<221> NAME/KEY: CDS
<222> LOCATION: (13)..(2757)

<400> SEQUENCE: 6
agcgtcggga cc atg gat tgg gat tgg ggg aac cgc tgc agc cgc ccg gga    51
              Met Asp Trp Asp Trp Gly Asn Arg Cys Ser Arg Pro Gly
                1               5                  10 cgg cgg gac ctg ctg tgc gtg ctg gca ctg ctc gcc ggc tgt ctg ctc      99
Arg Arg Asp Leu Leu Cys Val Leu Ala Leu Leu Ala Gly Cys Leu Leu
         15                  20                  25 ccg gta tgc cgg acg cgc gtc tac acc aac cac tgg gca gtg aag atc    147
Pro Val Cys Arg Thr Arg Val Tyr Thr Asn His Trp Ala Val Lys Ile
 30                  35                  40                  45 gcc ggc ggc ttc gcg gag gca gat cgc ata gcc agc aag tac gga ttc    195
Ala Gly Gly Phe Ala Glu Ala Asp Arg Ile Ala Ser Lys Tyr Gly Phe
                 50                  55                  60 atc aac gta gga cag atc ggt gca ctg aag gac tat tat cac ttc tac    243
Ile Asn Val Gly Gln Ile Gly Ala Leu Lys Asp Tyr Tyr His Phe Tyr
             65                  70                  75 cat agt agg acc att aaa agg tct gtt ctc tcg agc aga gga acc cac    291
His Ser Arg Thr Ile Lys Arg Ser Val Leu Ser Ser Arg Gly Thr His
         80                  85                  90 agt ttc att tca atg gaa cca aag gtg gag tgg atc caa cag caa gtg    339
Ser Phe Ile Ser Met Glu Pro Lys Val Glu Trp Ile Gln Gln Gln Val
     95                 100                 105 gtg aaa aaa aga acc aag agg gat tat gac ctc agc cat gcc cag tca    387
Val Lys Lys Arg Thr Lys Arg Asp Tyr Asp Leu Ser His Ala Gln Ser
110                 115                 120                 125 acc tac ttc aat gat ccc aag tgg cca agt atg tgg tac atg cac tgt    435
Thr Tyr Phe Asn Asp Pro Lys Trp Pro Ser Met Trp Tyr Met His Cys
                130                 135                 140 agc gac aat aca cat ccc tgc cag tct gac atg aat atc gaa gga gcc    483
Ser Asp Asn Thr His Pro Cys Gln Ser Asp Met Asn Ile Glu Gly Ala
            145                 150                 155 tgg aag aga ggc tac acg gga aag aac att gtg gtc act atc ctg gat    531
```

```
                                                        -continued

Trp Lys Arg Gly Tyr Thr Gly Lys Asn Ile Val Val Thr Ile Leu Asp
        160                 165                 170 gac gga att gag aga acc cat cca gat ctg atg caa aac tac gat gct       579
Asp Gly Ile Glu Arg Thr His Pro Asp Leu Met Gln Asn Tyr Asp Ala
    175                 180                 185 ctg gca agt tgc gac gtg aat ggg aat gac ttg gac cca atg cct cgt       627
Leu Ala Ser Cys Asp Val Asn Gly Asn Asp Leu Asp Pro Met Pro Arg
190                 195                 200                 205 tat gat gca agc aac gag aac aag cat ggg act cgc tgt gct gga gaa       675
Tyr Asp Ala Ser Asn Glu Asn Lys His Gly Thr Arg Cys Ala Gly Glu
                210                 215                 220 gtg gca gcc gct gca aac aat tcg cac tgc aca gtc gga att gct ttc       723
Val Ala Ala Ala Ala Asn Asn Ser His Cys Thr Val Gly Ile Ala Phe
            225                 230                 235 aac gcc aag atc gga gga gtg cga atg ctg gac gga gat gtc acg gac       771
Asn Ala Lys Ile Gly Gly Val Arg Met Leu Asp Gly Asp Val Thr Asp
        240                 245                 250 atg gtt gaa gca aaa tca gtt agc ttc aac ccc cag cac gtg cac att       819
Met Val Glu Ala Lys Ser Val Ser Phe Asn Pro Gln His Val His Ile
    255                 260                 265 tac agc gcc agc tgg ggc ccg gat gat gat ggc aag act gtg gac gga       867
Tyr Ser Ala Ser Trp Gly Pro Asp Asp Asp Gly Lys Thr Val Asp Gly
270                 275                 280                 285 cca gcc ccc ctc acc cgg caa gcc ttt gaa aac ggc gtt aga atg ggg       915
Pro Ala Pro Leu Thr Arg Gln Ala Phe Glu Asn Gly Val Arg Met Gly
                290                 295                 300 cgg aga ggc ctc ggc tct gtg ttt gtt tgg gca tct gga aat ggt gga       963
Arg Arg Gly Leu Gly Ser Val Phe Val Trp Ala Ser Gly Asn Gly Gly
            305                 310                 315 agg agc aaa gac cac tgc tcc tgt gat ggc tac acc aac agc atc tac      1011
Arg Ser Lys Asp His Cys Ser Cys Asp Gly Tyr Thr Asn Ser Ile Tyr
        320                 325                 330 acc atc tcc atc agc agc act gca gaa agc gga aag aaa cct tgg tac      1059
Thr Ile Ser Ile Ser Ser Thr Ala Glu Ser Gly Lys Lys Pro Trp Tyr
    335                 340                 345 ctg gaa gag tgt tca tcc acg ctg gcc aca acc tac agc agc ggg gag      1107
Leu Glu Glu Cys Ser Ser Thr Leu Ala Thr Thr Tyr Ser Ser Gly Glu
350                 355                 360                 365 tcc tac gat aag aaa atc atc act aca gat ctg agg cag cgt tgc acg      1155
Ser Tyr Asp Lys Lys Ile Ile Thr Thr Asp Leu Arg Gln Arg Cys Thr
                370                 375                 380 gac aac cac act ggg acg tca gcc tca gcc ccc atg gct gca ggc atc      1203
Asp Asn His Thr Gly Thr Ser Ala Ser Ala Pro Met Ala Ala Gly Ile
            385                 390                 395 att gcg ctg gcc ctg gaa gcc aat ccg ttt ctg acc tgg aga gac gta      1251
Ile Ala Leu Ala Leu Glu Ala Asn Pro Phe Leu Thr Trp Arg Asp Val
        400                 405                 410 cag cat gtt att gtc agg act tcc cgt gcg gga cat ttg aac gct aat      1299
Gln His Val Ile Val Arg Thr Ser Arg Ala Gly His Leu Asn Ala Asn
    415                 420                 425 gac tgg aaa acc aat gct gct ggt ttt aag gtg agc cat ctt tat gga      1347
Asp Trp Lys Thr Asn Ala Ala Gly Phe Lys Val Ser His Leu Tyr Gly
430                 435                 440                 445 ttt gga ctg atg gac gca gaa gcc atg gtg atg gag gca gag aag tgg      1395
Phe Gly Leu Met Asp Ala Glu Ala Met Val Met Glu Ala Glu Lys Trp
                450                 455                 460 acc acc gtt ccc cgg cag cac gtg tgt gtg gag agc aca gac cga caa      1443
Thr Thr Val Pro Arg Gln His Val Cys Val Glu Ser Thr Asp Arg Gln
            465                 470                 475
```

```
atc aag aca atc cgc cct aac agt gca gtg cgc tcc atc tac aaa gct    1491
Ile Lys Thr Ile Arg Pro Asn Ser Ala Val Arg Ser Ile Tyr Lys Ala
        480                 485                 490 tca ggc tgc tcg gat aac ccc aac cgc cat gtc aac tac ctg gag cac    1539
Ser Gly Cys Ser Asp Asn Pro Asn Arg His Val Asn Tyr Leu Glu His
495                 500                 505 gtc gtt gtg cgc atc acc atc acc cac ccc agg aga gga gac ctg gcc    1587
Val Val Val Arg Ile Thr Ile Thr His Pro Arg Arg Gly Asp Leu Ala
510                 515                 520                 525 atc tac ctg acc tcg ccc tct gga act agg tct cag ctt ttg gcc aac    1635
Ile Tyr Leu Thr Ser Pro Ser Gly Thr Arg Ser Gln Leu Leu Ala Asn
                530                 535                 540 agg cta ttt gat cac tcc atg gaa gga ttc aaa aac tgg gag ttc atg    1683
Arg Leu Phe Asp His Ser Met Glu Gly Phe Lys Asn Trp Glu Phe Met
            545                 550                 555 acc att cat tgc tgg gga gaa aga gct gct ggt gac tgg gtc ctt gaa    1731
Thr Ile His Cys Trp Gly Glu Arg Ala Ala Gly Asp Trp Val Leu Glu
        560                 565                 570 gtt tat gat act ccc tct cag cta agg aac ttt aag act cca ggt aaa    1779
Val Tyr Asp Thr Pro Ser Gln Leu Arg Asn Phe Lys Thr Pro Gly Lys
575                 580                 585 ttg aaa gaa tgg tct ttg gtc ctc tac ggc acc tcc gtg cgg cca tat    1827
Leu Lys Glu Trp Ser Leu Val Leu Tyr Gly Thr Ser Val Arg Pro Tyr
590                 595                 600                 605 tca cca acc aat gaa ttt ccg aaa gtg gaa cgg ttc cgc tat agc cga    1875
Ser Pro Thr Asn Glu Phe Pro Lys Val Glu Arg Phe Arg Tyr Ser Arg
                610                 615                 620 gtt gaa gac ccc aca gac gac tat ggc aca gag gat tat gca ggt ccc    1923
Val Glu Asp Pro Thr Asp Asp Tyr Gly Thr Glu Asp Tyr Ala Gly Pro
            625                 630                 635 tgc gac cct gag tgc agt gag gtt ggc tgt gac ggg cca gga cca gac    1971
Cys Asp Pro Glu Cys Ser Glu Val Gly Cys Asp Gly Pro Gly Pro Asp
        640                 645                 650 cac tgc aat gac tgt ttg cac tac tac tac aag ctg aaa aac aat acc    2019
His Cys Asn Asp Cys Leu His Tyr Tyr Tyr Lys Leu Lys Asn Asn Thr
    655                 660                 665 agg atc tgt gtc tcc agc tgc ccc cct ggc cac tac cac gcc gac aag    2067
Arg Ile Cys Val Ser Ser Cys Pro Pro Gly His Tyr His Ala Asp Lys
670                 675                 680                 685 aag cgc tgc agg aag tgt gcc ccc aac tgt gag tcc tgc ttt ggg agc    2115
Lys Arg Cys Arg Lys Cys Ala Pro Asn Cys Glu Ser Cys Phe Gly Ser
                690                 695                 700 cat ggt gac caa tgc atg tcc tgc aaa tat gga tac ttt ctg aat gaa    2163
His Gly Asp Gln Cys Met Ser Cys Lys Tyr Gly Tyr Phe Leu Asn Glu
            705                 710                 715 gaa acc aac agc tgt gtt act cac tgc cct gat ggg tca tat cag gat    2211
Glu Thr Asn Ser Cys Val Thr His Cys Pro Asp Gly Ser Tyr Gln Asp
        720                 725                 730 acc aag aaa aat ctt tgc cgg aaa tgc agt gaa aac tgc aag aca tgt    2259
Thr Lys Lys Asn Leu Cys Arg Lys Cys Ser Glu Asn Cys Lys Thr Cys
    735                 740                 745 act gaa ttc cat aac tgt aca gaa tgt agg gat ggg tta agc ctg cag    2307
Thr Glu Phe His Asn Cys Thr Glu Cys Arg Asp Gly Leu Ser Leu Gln
750                 755                 760                 765 gga tcc cgg tgc tct gtc tcc tgt gaa gat gga cgg tat ttc aac ggc    2355
Gly Ser Arg Cys Ser Val Ser Cys Glu Asp Gly Arg Tyr Phe Asn Gly
                770                 775                 780 cag gac tgc cag ccc tgc cac cgc ttc tgc gcc act tgt gct ggg gca    2403
Gln Asp Cys Gln Pro Cys His Arg Phe Cys Ala Thr Cys Ala Gly Ala
            785                 790                 795
```

```
gga gct gat ggg tgc att aac tgc aca gag ggc tac ttc atg gag gat      2451
Gly Ala Asp Gly Cys Ile Asn Cys Thr Glu Gly Tyr Phe Met Glu Asp
            800                 805                 810 ggg aga tgc gtg cag agc tgt agt atc agc tat tac ttt gac cac tct      2499
Gly Arg Cys Val Gln Ser Cys Ser Ile Ser Tyr Tyr Phe Asp His Ser
        815                 820                 825 tca gag aat gga tac aaa tcc tgc aaa aaa tgt gat atc agt tgt ttg      2547
Ser Glu Asn Gly Tyr Lys Ser Cys Lys Lys Cys Asp Ile Ser Cys Leu
830                 835                 840                 845 acg tgc aat ggc cca gga ttc aag aac tgt aca agc tgc cct agt ggg      2595
Thr Cys Asn Gly Pro Gly Phe Lys Asn Cys Thr Ser Cys Pro Ser Gly
                850                 855                 860 tat ctc tta gac tta gga atg tgt caa atg gga gcc att tgc aag gat      2643
Tyr Leu Leu Asp Leu Gly Met Cys Gln Met Gly Ala Ile Cys Lys Asp
            865                 870                 875 gca acg gaa gag tcc tgg gcg gaa gga ggc ttc tgt atg ctt gtg aaa      2691
Ala Thr Glu Glu Ser Trp Ala Glu Gly Gly Phe Cys Met Leu Val Lys
        880                 885                 890 aag aac aat ctg tgc caa cgg aag gtt ctt caa caa ctt tgc tgc aaa      2739
Lys Asn Asn Leu Cys Gln Arg Lys Val Leu Gln Gln Leu Cys Cys Lys
895                 900                 905 aca tgt aca ttc caa ggc tgagcagcc                                    2766
Thr Cys Thr Phe Gln Gly
910                 915

<210> SEQ ID NO 7
<211> LENGTH: 915
<212> TYPE: PRT
<213> ORGANISM: Homo sapiens

<400> SEQUENCE: 7

Met Asp Trp Asp Trp Gly Asn Arg Cys Ser Arg Pro Gly Arg Arg Asp
 1               5                  10                  15

Leu Leu Cys Val Leu Ala Leu Leu Ala Gly Cys Leu Leu Pro Val Cys
                20                  25                  30

Arg Thr Arg Val Tyr Thr Asn His Trp Ala Val Lys Ile Ala Gly Gly
            35                  40                  45

Phe Ala Glu Ala Asp Arg Ile Ala Ser Lys Tyr Gly Phe Ile Asn Val
        50                  55                  60

Gly Gln Ile Gly Ala Leu Lys Asp Tyr Tyr His Phe Tyr His Ser Arg
65                  70                  75                  80

Thr Ile Lys Arg Ser Val Leu Ser Ser Arg Gly Thr His Ser Phe Ile
                85                  90                  95

Ser Met Glu Pro Lys Val Glu Trp Ile Gln Gln Val Val Lys Lys
                100                 105                 110

Arg Thr Lys Arg Asp Tyr Asp Leu Ser His Ala Gln Ser Thr Tyr Phe
            115                 120                 125

Asn Asp Pro Lys Trp Pro Ser Met Trp Tyr Met His Cys Ser Asp Asn
        130                 135                 140

Thr His Pro Cys Gln Ser Asp Met Asn Ile Glu Gly Ala Trp Lys Arg
145                 150                 155                 160

Gly Tyr Thr Gly Lys Asn Ile Val Val Thr Ile Leu Asp Asp Gly Ile
                165                 170                 175

Glu Arg Thr His Pro Asp Leu Met Gln Asn Tyr Asp Ala Leu Ala Ser
            180                 185                 190

Cys Asp Val Asn Gly Asn Asp Leu Asp Pro Met Pro Arg Tyr Asp Ala
        195                 200                 205
```

-continued

```
Ser Asn Glu Asn Lys His Gly Thr Arg Cys Ala Gly Glu Val Ala Ala
210                 215                 220

Ala Ala Asn Asn Ser His Cys Thr Val Gly Ile Ala Phe Asn Ala Lys
225                 230                 235                 240

Ile Gly Gly Val Arg Met Leu Asp Gly Asp Val Thr Asp Met Val Glu
            245                 250                 255

Ala Lys Ser Val Ser Phe Asn Pro Gln His Val His Ile Tyr Ser Ala
                260                 265                 270

Ser Trp Gly Pro Asp Asp Gly Lys Thr Val Asp Gly Pro Ala Pro
            275                 280                 285

Leu Thr Arg Gln Ala Phe Glu Asn Gly Val Arg Met Gly Arg Arg Gly
290                 295                 300

Leu Gly Ser Val Phe Val Trp Ala Ser Gly Asn Gly Gly Arg Ser Lys
305                 310                 315                 320

Asp His Cys Ser Cys Asp Gly Tyr Thr Asn Ser Ile Tyr Thr Ile Ser
                325                 330                 335

Ile Ser Ser Thr Ala Glu Ser Gly Lys Lys Pro Trp Tyr Leu Glu Glu
            340                 345                 350

Cys Ser Ser Thr Leu Ala Thr Thr Tyr Ser Ser Gly Glu Ser Tyr Asp
                355                 360                 365

Lys Lys Ile Ile Thr Thr Asp Leu Arg Gln Arg Cys Thr Asp Asn His
370                 375                 380

Thr Gly Thr Ser Ala Ser Ala Pro Met Ala Ala Gly Ile Ile Ala Leu
385                 390                 395                 400

Ala Leu Glu Ala Asn Pro Phe Leu Thr Trp Arg Asp Val Gln His Val
                405                 410                 415

Ile Val Arg Thr Ser Arg Ala Gly His Leu Asn Ala Asn Asp Trp Lys
            420                 425                 430

Thr Asn Ala Ala Gly Phe Lys Val Ser His Leu Tyr Gly Phe Gly Leu
                435                 440                 445

Met Asp Ala Glu Ala Met Val Met Glu Ala Glu Lys Trp Thr Thr Val
        450                 455                 460

Pro Arg Gln His Val Cys Val Glu Ser Thr Asp Arg Gln Ile Lys Thr
465                 470                 475                 480

Ile Arg Pro Asn Ser Ala Val Arg Ser Ile Tyr Lys Ala Ser Gly Cys
                485                 490                 495

Ser Asp Asn Pro Asn Arg His Val Asn Tyr Leu Glu His Val Val Val
                500                 505                 510

Arg Ile Thr Ile Thr His Pro Arg Arg Gly Asp Leu Ala Ile Tyr Leu
            515                 520                 525

Thr Ser Pro Ser Gly Thr Arg Ser Gln Leu Leu Ala Asn Arg Leu Phe
530                 535                 540

Asp His Ser Met Glu Gly Phe Lys Asn Trp Glu Phe Met Thr Ile His
545                 550                 555                 560

Cys Trp Gly Glu Arg Ala Ala Gly Asp Trp Val Leu Glu Val Tyr Asp
                565                 570                 575

Thr Pro Ser Gln Leu Arg Asn Phe Lys Thr Pro Gly Lys Leu Lys Glu
                580                 585                 590

Trp Ser Leu Val Leu Tyr Gly Thr Ser Val Arg Pro Tyr Ser Pro Thr
            595                 600                 605

Asn Glu Phe Pro Lys Val Glu Arg Phe Arg Tyr Ser Arg Val Glu Asp
610                 615                 620
```

-continued

```
Pro Thr Asp Asp Tyr Gly Thr Glu Asp Tyr Ala Gly Pro Cys Asp Pro
625                 630                 635                 640

Glu Cys Ser Glu Val Gly Cys Asp Gly Pro Gly Pro Asp His Cys Asn
            645                 650                 655

Asp Cys Leu His Tyr Tyr Lys Leu Lys Asn Asn Thr Arg Ile Cys
            660                 665                 670

Val Ser Ser Cys Pro Pro Gly His Tyr His Ala Asp Lys Lys Arg Cys
            675                 680                 685

Arg Lys Cys Ala Pro Asn Cys Glu Ser Cys Phe Gly Ser His Gly Asp
        690                 695                 700

Gln Cys Met Ser Cys Lys Tyr Gly Tyr Phe Leu Asn Glu Glu Thr Asn
705                 710                 715                 720

Ser Cys Val Thr His Cys Pro Asp Gly Ser Tyr Gln Asp Thr Lys Lys
            725                 730                 735

Asn Leu Cys Arg Lys Cys Ser Glu Asn Cys Lys Thr Cys Thr Glu Phe
            740                 745                 750

His Asn Cys Thr Glu Cys Arg Asp Gly Leu Ser Leu Gln Gly Ser Arg
            755                 760                 765

Cys Ser Val Ser Cys Glu Asp Gly Arg Tyr Phe Asn Gly Gln Asp Cys
770                 775                 780

Gln Pro Cys His Arg Phe Cys Ala Thr Cys Ala Gly Ala Gly Ala Asp
785                 790                 795                 800

Gly Cys Ile Asn Cys Thr Glu Gly Tyr Phe Met Glu Asp Gly Arg Cys
            805                 810                 815

Val Gln Ser Cys Ser Ile Ser Tyr Tyr Phe Asp His Ser Ser Glu Asn
            820                 825                 830

Gly Tyr Lys Ser Cys Lys Lys Cys Asp Ile Ser Cys Leu Thr Cys Asn
            835                 840                 845

Gly Pro Gly Phe Lys Asn Cys Thr Ser Cys Pro Ser Gly Tyr Leu Leu
        850                 855                 860

Asp Leu Gly Met Cys Gln Met Gly Ala Ile Cys Lys Asp Ala Thr Glu
865                 870                 875                 880

Glu Ser Trp Ala Glu Gly Gly Phe Cys Met Leu Val Lys Lys Asn Asn
                885                 890                 895

Leu Cys Gln Arg Lys Val Leu Gln Leu Cys Cys Lys Thr Cys Thr
            900                 905                 910

Phe Gln Gly
        915
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8
ccaagcttgg ctgctgtgcg tgctggc                                27

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

```
<400> SEQUENCE: 9
ctgcctcaga tctgtagtg                                                        19
```